US005635103A

United States Patent [19]
Willey et al.

[11] Patent Number: 5,635,103
[45] Date of Patent: Jun. 3, 1997

[54] BLEACHING COMPOSITIONS AND ADDITIVES COMPRISING BLEACH ACTIVATORS HAVING ALPHA-MODIFIED LACTAM LEAVING-GROUPS

[75] Inventors: Alan D. Willey; Kevin L. Kott, both of Cincinnati; Gregory S. Miracle, Hamilton; Eugene P. Gosselink; James C. T. R. B. St. Laurent, both of Cincinnati, all of Ohio

[73] Assignee: The Procter & Gamble Company, Cincinnati, Ohio

[21] Appl. No.: 375,761

[22] Filed: Jan. 20, 1995

[51] Int. Cl.$^6$ .................... A01N 43/84; C11D 3/28; C11D 3/395

[52] U.S. Cl. .................. 510/313; 8/111; 252/186.39; 540/485; 540/575; 544/106; 544/176; 548/544

[58] Field of Search .................. 8/111; 252/102, 252/186.38, 186.39, 524, 542; 540/485, 575; 544/106, 176; 548/544

[56] References Cited

U.S. PATENT DOCUMENTS

| | | | |
|---|---|---|---|
| 3,042,621 | 7/1962 | Kirschenbauer | 252/99 |
| 3,075,921 | 1/1963 | Brocklehurst et al. | 252/99 |
| 3,133,048 | 5/1964 | Moore | 525/154 |
| 3,177,148 | 4/1965 | Bright et al. | 252/99 |
| 3,637,339 | 1/1972 | Gray | 8/111 |
| 3,775,332 | 11/1973 | Heins et al. | 252/95 |
| 3,812,247 | 5/1974 | Heinz et al. | 424/62 |
| 3,912,770 | 10/1975 | Botta | 554/101 |
| 4,013,575 | 3/1977 | Castrantas et al. | 252/104 |
| 4,126,614 | 11/1978 | Suzuki | 562/567 |
| 4,153,582 | 5/1979 | Puffr | 252/511 |
| 4,207,199 | 6/1980 | Perner | 252/174.23 |
| 4,545,784 | 10/1985 | Sanderson | 8/107 |
| 4,551,263 | 11/1985 | Schellhammer | 252/186.39 |
| 4,663,641 | 5/1987 | Iiyama | 346/204 |
| 4,665,410 | 5/1987 | Iiyama | 346/204 |
| 4,778,618 | 10/1988 | Fong et al. | 252/186.23 |
| 4,790,952 | 12/1988 | Steichen et al. | 252/186.39 |
| 4,931,562 | 6/1990 | Akabane | 546/19 |
| 5,155,100 | 10/1992 | Erion | 514/119 |
| 5,349,045 | 9/1994 | Yokomori | 435/115 |

FOREIGN PATENT DOCUMENTS

| | | | |
|---|---|---|---|
| 0257700 | 3/1988 | European Pat. Off. | C11D 3/39 |
| 439766 | 12/1990 | European Pat. Off. | C07D 207/27 |
| 3217373 | 11/1983 | Germany | C07D 222/10 |
| 2-115154 | 4/1990 | Japan | C07C 237/52 |
| 2-182793 | 7/1990 | Japan | C11D 1/831 |
| 4-164056 | 6/1992 | Japan | C07C 237/52 |
| WO93/12067 | 6/1993 | WIPO | C07C 69/66 |
| WO93/20167 | 10/1993 | WIPO | C09K 3/00 |
| WO94/18298 | 8/1994 | WIPO | C11D 3/39 |
| WO94/18299 | 8/1994 | WIPO | C11D 3/39 |
| WO94/28103 | 12/1994 | WIPO | C11D 3/39 |
| WO95/00626 | 1/1995 | WIPO | C11D 3/39 |

OTHER PUBLICATIONS

Kirk Othmer, Encyclopedia of Chemical Technology, vol. 7, 4th Ed., 1993, pp. 1072–1117.
Kirk Othmer, Encyclopedia of Chemical Technology, vol. 4, 4th Ed., 1994, pp. 271–300.
Kirk Othmer, Encyclopedia of Chemical Technology, vol. 9, 4th Ed., 1993, pp. 567–620.
Padwa et al., "Studies on the Intramolecular Cycloaddition Reaction of Mesoionics Derived from the Rhodium (II)–Catalyzed Cyclization of Diazoimides", J. Org. Chem 1994, 59 (1418–1427), Jan. 3, 1994.

*Primary Examiner*—Dennis Albrecht
*Attorney, Agent, or Firm*—M. D. Jones; B. M. Bolam; K. W. Zerby

[57] ABSTRACT

Improved cleaning and/or bleaching compositions including fabric laundry and bleaching compositions, automatic dishwashing compositions, hard surface cleaners, bleach additives and the like, suitable for domestic use, comprising improved bleach activators having particular alpha-modified lactam leaving groups leading to improved in-use performance of bleaching agents such as perborate even under wash conditions less alkaline than those typically encountered or when hydrogen peroxide source is at low levels in a cleaning operation. A preferred class of activators are N-acyl-3-morpholinone compounds with benzoyl being a preferred acyl group and N-Benzoyl-3-oxomorpholine being a highly preferred activator.

15 Claims, No Drawings

BLEACHING COMPOSITIONS AND ADDITIVES COMPRISING BLEACH ACTIVATORS HAVING ALPHA-MODIFIED LACTAM LEAVING-GROUPS

FIELD OF THE INVENTION

The present invention relates to improved cleaning and/or bleaching compositions including fabric laundry and bleaching compositions, automatic dishwashing compositions, hard surface cleaners, bleach additives and the like. The bleaching compositions comprise selected bleach activators having particular alpha-modified lactam leaving-groups. The activators improve the in-use performance of bleaching agents such as perborate, even under wash conditions less alkaline than those typical of the art, or even when hydrogen peroxide is present at only low levels.

BACKGROUND OF THE INVENTION

The formulation of detergent compositions which effectively remove a wide variety of soils and stains from fabrics under wide-ranging use conditions remains a considerable challenge to the laundry detergent industry. Unsolved problems similarly exist for the formulator of automatic dishwashing detergent compositions (ADD's). These compositions are expected to efficiently cleanse and sanitize dishware, often under heavier soil loads. The problems associated with the formulation of truly effective cleaning and bleaching compositions for use by the consumer have been exacerbated by legislation which limits the use of effective ingredients such as phosphate builders in many regions of the world.

Most conventional cleaning compositions contain mixtures of detersive surfactants to remove a wide variety of soils and stains from surfaces. In addition, detersive enzymes, soil suspending agents, builders, brighteners, and the like may be added to boost overall cleaning. Many fully-formulated cleaning compositions contain oxygen bleach, especially as hydrogen peroxide, typical sources for which include perborate or percarbonate salts. While quite effective at high temperatures, high levels and high pH's, hydrogen peroxide loses much of its bleaching function at low to moderate temperatures, low to moderate perborate/percarbonate levels and/or low to moderate wash pH. Yet all of these are increasingly favored in consumer product use.

Various bleach activators such as tetraacetylethylenediamine (TAED) and nonanoyloxybenzenesulfonate (NOBS) have been developed to potentiate the bleaching action of perborate and percarbonate across a wide temperature range. NOBS is particularly effective on "dingy" fabrics.

A limitation with activators such as the widely commercialized TAED is that the wash solution or liquor should have a pH of about 10 or higher for best results. Since soils, especially from foods, are often acidic, detergent products are frequently quite alkaline or are buffered sufficiently to maintain a high pH so the bleach activator system can operate effectively throughout the wash. However, this need runs counter to providing milder formulations which could be improved in their compatibility with fabrics, glassware and/or skin. In cleaning operations below pH 10, on the other hand, many of the existing bleach activators lose their effectiveness or undergo competing side reactions which tend to produce ineffective byproducts.

The search, therefore, continues for more effective activator materials, especially for use in mildly alkaline washing liquors or with decreased levels of perborate or other sources of hydrogen peroxide. Improved activator materials should be safe, effective, and will preferably be designed to interact with troublesome soils and stains. Various activators have been described in the literature. Many are esoteric and expensive.

It has now been determined that certain selected bleach activators are unexpectedly effective in removing soils and stains from fabrics and hard surfaces such as dishes even under low alkaline wash conditions or with decreased levels of hydrogen peroxide source materials. The preferred activators also have advantageously high ratios of rates of perhydrolysis to hydrolysis and of perhydrolysis to diacylperoxide formation. Without being limited by theory, these unusual rate ratios lead to a number of significant benefits for the instant activators, including increased efficiency, avoidance of wasteful byproduct formation in the wash, increased color compatibility, increased enzyme compatibility, and better stability on storage.

When formulated as described herein, cleaning and/or bleaching compositions, including detergent compositions, are provided using the selected bleach activators to remove soils and stains not only from fabrics, but also from dishware in automatic dishwashing compositions, from kitchen and bathroom hard surfaces, and the like, with excellent results. Advantages of these embodiments include excellent performance at typical wash pH's, e.g., about 10, as well as unexpectedly superior performance at moderate wash pH, typically from about 7 to about 9. Also secured herein are novel activators designed to function well over a wide range of wash pH and hydrogen peroxide source levels. In short, the present cleaning/bleaching compositions and improved bleach activators, as further illustrated in the disclosure hereinafter, provide a substantial advance over those of the art.

BACKGROUND ART

Bleach activators of various types are described in U.S. Pat. Nos. 4,545,784; 4,013,575; 3,075,921; 3,637,339; 3,177,148; 3,042,621; 3,812,247; 3,775,332; 4,778,618; 4,790,952; EP 257,700; WO 94/18299; WO 94/18298; WO 93/20167; WO 93/12067; and in JP 02115154. Other references include Aikawa CA 85:1086z; Stehlicek CA 108:187402w; Ishida CA 88:169981y; Kirk Othmer, Encyclopedia of Chemical Technology, Vol. 7, 4th Ed., 1993, pp. 1072–1117; Kirk Othmer, Encyclopedia of Chemical Technology, Vol. 4, 4th Ed., 1994, pp. 271–299; Kirk Othmer, Encyclopedia of Chemical Technology, Vol. 9, 4th Ed., 1993, pp. 567–620.

SUMMARY OF THE INVENTION

The present invention relates to cleaning compositions comprising selected bleach activators, more specifically, a class of particularly effective and efficient bleach activators herein referred to as alpha-modified lactam bleach activators, or simply, "alpha-modified lactams". The compositions encompass bleach additives and bleaching compositions and are useful in the home for treatment of fabrics and hard surfaces.

The term "bleach activator" refers to a compound which reacts with hydrogen peroxide or its anion to form a more effective oxidant. Known bleach activators include perhydrolyzable acyl compounds having a leaving group such as oxybenzenesulfonate.

Alpha-modified lactam bleach activators or simply "alpha-modified lactams" for the purposes of the cleaning compositions and additives of the present invention comprise at least one lactam moiety having ring size 5 to 8 wherein the constitution of the alpha atom is modified. The term "constitution" is defined by Eliel et al, Stereochemistry of Organic Compounds, Wiley-Interscience, 1994, p. 13, incorporated by reference. Alpha-modified six-membered lactams are compared with the corresponding "unmodified" form as follows:

Modified:

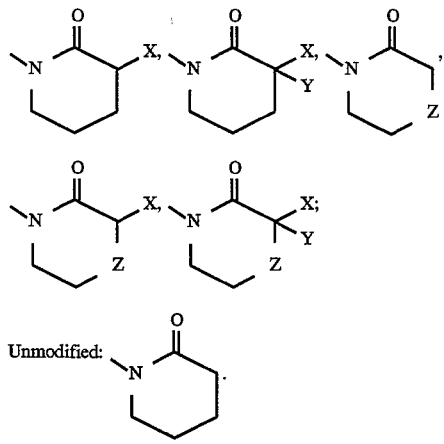

Unmodified:

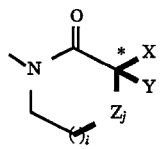

The alpha-modified lactams as defined herein encompass both exocyclically substituted lactams and substituted or non-substituted lactams which contain a hetero-atom in the selected endocyclic position which is indicated by Z. At least one alpha-modified lactam moiety functions as the leaving-group in any bleach activator herein. In general, there may be more than one such moiety in an alpha modified lactam bleach activator.

Cleaning compositions herein generally comprise an effective amount of the alpha-modified lactam bleach activator. By "effective amount" herein is meant an amount which is sufficient, under whatever comparative test conditions are employed, to enhance cleaning of a soiled surface. In general the level of alpha-modified lactam may vary widely, for example up to 90% or more, by weight, more typically from about 0.1% to about 70% by weight of the composition. In many cleaning compositions herein, such as fully-formulated granular laundry detergents, typical levels of alpha-modified lactam can be lower, e.g., from about 0.1% to about 30%, more preferably from about 0.1% to about 10%, more preferably still from about 0.5% to about 5% of the cleaning composition.

In more detail the present cleaning compositions comprise an alpha-modified lactam bleach activator having at least one leaving-group, L, having the cyclic structure:

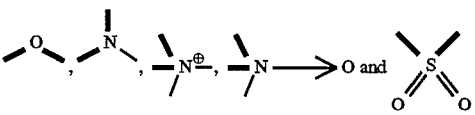
(I)

wherein: i and j are integers; i is from 0 to 3; j is 0 or 1 provided that when i is 0, j is 1; Z is selected from

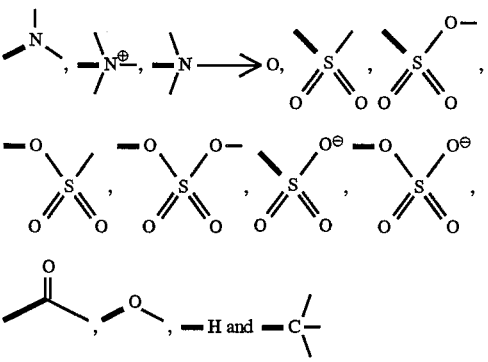

wherein any Z covalently connects through two valencies forming part of said cyclic structure; and at least one of X and Y is selected from —Cl, —Br, —NO$_2$, —CN, wherein one valency of any X and Y covalently connects said X and Y to said cyclic structure; and further provided that when j is 0, at least one of X and Y is different from H.

Cleaning compositions comprising alpha-modified lactam bleach activators having more than one lactam leaving-group, for example two or three such leaving-groups, are likewise within the present invention. Such activators can readily be arrived at through the use of bifunctional reagents such as alkyl dihalides.

Cleaning compositions herein may also comprise alpha-modified lactam bleach activators wherein X and Y, X and Z, and/or Y and Z are covalently linked to form a spirocyclic, fused bicyclic or tricyclic moiety. In general, such structures are not highly preferred due to cost and synthetic complexity.

Simple, but highly preferred embodiments of the present cleaning compositions comprise an alpha-modified lactam RC(O)L wherein R comprises more than two carbon atoms. More generally, the R moiety in such activators may vary widely according to the desires of the formulator: thus, when a greater degree of surface activity is desired, R can be a fatty alkyl moiety; when an activator especially suited for use at lower pH's is desired, R can be an electron-withdrawing moiety; and when a high degree of solubility is desired, R can contain a charged or noncharged solubilizing moiety, such as quaternary ammonium or polyoxyalkylene moieties, respectively.

The cleaning or bleaching compositions of the invention fall in two broad groups: (a) those designed for self-contained, unassisted bleaching or stain removal—such compositions further comprise a source of hydrogen peroxide; and (b) those designed to be used as "bleach boosters" or "bleach additives"—such compositions may contain no built-in source of hydrogen peroxide. For case (b), hydrogen peroxide can be separately provided in the wash, for example it can be delivered through the use of a conventional detergent product.

The present alpha-modified lactam bleach activators are unexpectedly effective when in-wash levels of hydrogen peroxide are low, for example, when the level of the source of hydrogen peroxide is sufficient to provide a perhydroxyl ion concentration, as determined at a pH of about 7.5, of about $10^{-4}$ to about $10^{-10}$ molar.

Hydrogen peroxide source levels in the cleaning compositions can vary widely depending on the precise product application, typical levels being in the range from about 0.1% to about 70%, more preferably, from about 0.25% to about 25% of the total cleaning composition, on a weight basis.

In general, the pH of the instant compositions can vary widely. Thus, cleaning compositions herein can deliver wash pH's in the range from about 6 to about 13. More typically, the present cleaning compositions deliver an aqueous pH in the range from about 6.5 to about 9.5, more preferably from about 7.5 to about 8.5.

In preferred cleaning composition embodiments, there may also be present one or more members selected from the group consisting of: laundry detergent surfactants, low-foaming automatic dishwashing surfactants, bleach-stable thickeners and mixtures thereof. An example of a highly preferred suffactant is an ethoxylated nonionic surfactant. The compositions may or may not be formulated with a "brightener" or fluorescent whitening agent. Compositions may further comprise a transition-metal chelant. When organic solvents, such as alcohols, are present in the instant compositions, levels can vary consistently with use for aqueous cleaning purposes. In general such levels are preferably lower than those of organic solvents as used in dry-cleaning. In certain preferred embodiments, the compositions are substantially free from organic solvents of the types used in dry-cleaning operations.

An example of a cleaning composition of this invention which may be used as a "bleach additive" is one which comprises: from about 0.1% to about 30% of alpha-modified lactam bleach activator; from about 0.1% to about 60% of a nonionic surfactant; and from about 0.001% to about 10% of a transition-metal chelant.

An example of a cleaning composition of this invention having a "built-in" hydrogen peroxide source is one comprising: from about 0.1% to about 30% of alpha-modified lactam bleach activator; from about 0.1% to about 70% of a hydrogen peroxide source, such as sodium perborate monohydrate or sodium percarbonate; and from about 0.001% to about 10% of a transition-metal chelant.

A highly preferred bleach-additive or bleaching composition herein comprises from about 0.1% to about 10% of a bleach activator RC(O)L wherein R is a member selected from the group consisting of octyl, nonyl, 2,4,4-trimethylpentyl, 3-heptyl, decyl, phenyl, 3,5-dinitrophenyl, 3,5-dichlorophenyl, 4-(alkylsulfonyl)phenyl, 2-furyl, 3-furyl, 5-nitro-2-furyl and 5-nitro-3-furyl.

All percentages, ratios and proportions herein are by weight, unless otherwise specified. All documents cited are, in relevant part, incorporated herein by reference.

In the above structural representations and elsewhere herein except where specifically indicated, any non-bolded hyphens or lines as in —H or

are used to indicate potential bonding positions, or valences, to which any substituents may be attached, rather than to indicate methyl moieties as is sometimes done in Organic Chemistry. Heavy, or emphasized lines are reserved to indicate whether a particular moiety is connected into the alpha-modified lactam structure through one, or more valences.

DETAILED DESCRIPTION OF THE INVENTION

As noted, the present invention relates to cleaning compositions comprising alpha-modified lactam bleach activators. While alpha-modified lactam activators suitable for the practice of this invention may comprise more than one lactam moiety, the range of admissible structures is well illustrated using a simple alpha-modified lactam bleach activator of formula $R(C(O)L)_x$ wherein $x=1$ and L represents an alpha-modified lactam moiety. For this simple case, alpha-modified lactam bleach activators for the present cleaning compositions are further illustrated by the following compounds:

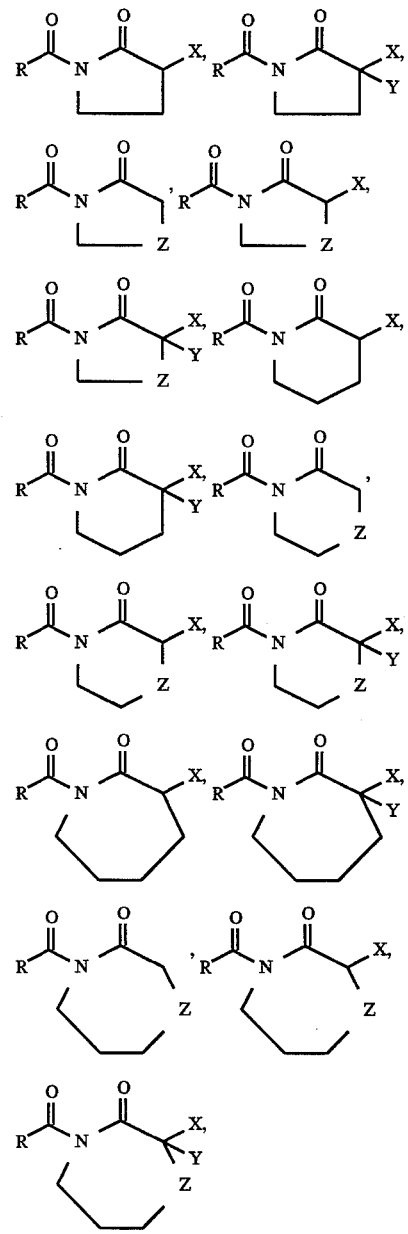

Each of these structures depicts an alpha-modified lactam bleach activator suitable for use in the cleaning compositions of the invention. For the purposes of the above illustration, Z is different from $CH_2$ and indicates a heteroatom, as noted. R, X, Y and Z are further illustrated in detail hereinafter.

Collectively, such preferred alpha-modified lactam bleach activators suitable for the instant cleaning compositions can be represented as follows wherein i and j have the values identified hereinbefore in the summary in connection with structure (I):

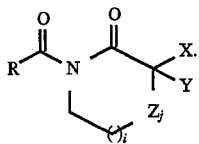

Alpha-modified lactam bleach activators herein can have any suitable physical form. Thus, crystalline or amorphous solids, oils and liquid forms of the bleach activators may be used.

Preferred cleaning compositions herein comprise an alpha-modified lactam bleach activator having a leaving group, L:

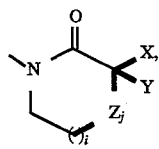

wherein i and j are as defined hereinabove, Z is selected from

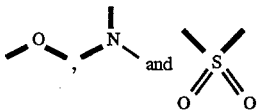

and at least one of X and Y is selected from —Cl, —Br, —NO$_2$, —CN,

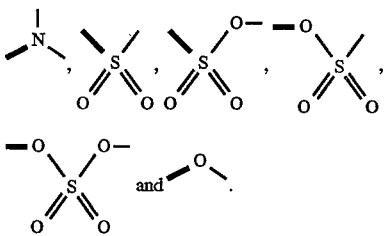

To further illustrate, each of X and Y in said alpha-modified lactam bleach activator can independently be selected from —Cl, —Br, —NO$_2$, —CN, —NR$^1_2$, —N$^+$R$^1_3$, —N$^+$O$^-$R$^1_2$, —(OSO$_2$R$^2$), —(SO$_2$OR$^2$), —(OSO$_2$OR$^2$), —(SO$_2$R$^2$), —(SO$_3^-$), —(OSO$_3^-$), —C(O)R$^3$, and —R$^3$; any R$^1$, when present, can be selected from —H, C$_1$–C$_4$ alkyl and benzyl; R$^2$, when present, is C$_1$–C$_9$ linear or branched alkyl, C$_7$–C$_{10}$ alkaryl or C$_7$–C$_{10}$ arylalkyl, and aryl; R$^3$, when present, is selected from —H, alkyl, alkaryl, aryl, alkoxy, aryloxy, and arylalkyloxy; and wherein Z, when present, is selected from —(O)—, —(NR$^1$)—, —(N$^+$R$^1_2$)—, —(N$^+$O$^-$R$^1$)— and —(SO$_2$)—. In general herein, arylalkyl can be replaced by alkylaryl or "alkaryl"; and arylalkyloxy can be replaced by alkaryloxy, unless otherwise noted.

It can be seen from the foregoing nonlimiting illustrations that the alpha-modified lactam bleach activator is envisaged to have either electron-withdrawing or electronegative substituents, such as —Cl, —Br, —NO$_2$, —CN etc., or relatively non-electron-withdrawing substituents, such as C$_1$–C$_4$ alkyl, in the alpha-modified lactam bleach activator. In the former instance, the resulting alpha-modified lactam bleach activator is highly preferred for moderate wash pH applications or applications in which perhydroxyl anion concentrations are relatively low. In the latter instance, having X and/or Y equal to methyl is highly preferred. Alpha-substituted lactam bleach activators having relatively non-electron-withdrawing substituents are more suited to higher wash pH applications.

Two preferred classes of alpha-modified lactam bleach activators are those wherein (a) j is 0, i is 2 or 3 and X is different from —H, alkyl and alkaryl; and (b) j is 1, i is 1 or 2 and Z is —O—.

When the X and/or Y substituents are electron-withdrawing or electronegative, then X and Y are preferably selected from —Cl, —Br, —NO$_2$, —NR$^1_2$, —N$^+$R$^1_3$, —SO$_2$R$^2$, —SO$_3$, alkoxy, aryloxy and arylalkyloxy. More preferably still, X and Y are selected from the group consisting of —NR$^1_2$, —N$^+$R$^1_3$, —SO$_2$R$^2$, —SO$_3^-$, alkoxy, aryloxy and arylalkyloxy. Most highly preferred are X and Y selected from the group consisting of —NR$^1_2$, —SO$_2$R$^2$, and —SO$_3^-$. When the X and Y substituents are relatively non-electron-withdrawing then X and Y are preferably selected from —H, alkyl, arylalkyl and alkaryl.

Highly preferred cleaning compositions comprise alpha-modified lactam bleach activators wherein L is a member selected from the group consisting of alpha-chlorocaprolactam, alpha-chlorovalerolactam, alpha, alpha-dichlorocaprolactam, alpha, alpha-dichlorovalerolactam, alpha-methoxycaprolactam, alpha-methoxyvalerolactam,

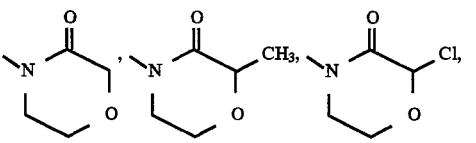

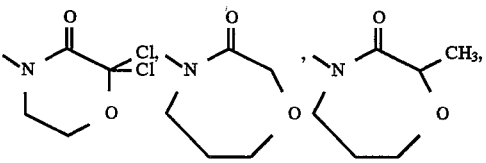

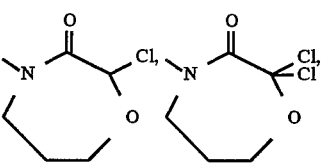

and mixtures thereof. Among the latter graphically presented structures, the following six are preferred:

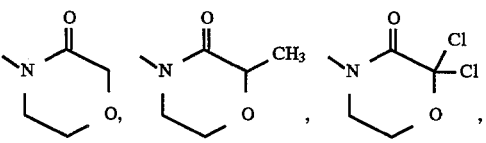

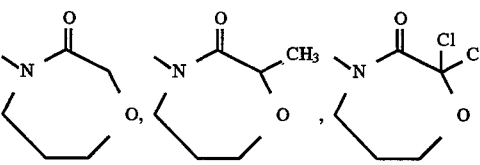

R in the alpha-modified lactam bleach activators herein may vary widely. For example, when the alpha-modified lactam bleach activators have formula RC(O)L, R is a monovalent moiety such as one selected from the group consisting of $C_3$–$C_{16}$ alkyl, alkaryl, aralkyl and aryl; said group encompassing linear, branched, saturated, unsaturated, substituted (for example, ethoxylated) and unsubstituted forms of said moieties. More preferably, such R is selected from the group consisting of phenyl, nitrophenyl, chlorophenyl, t-butylphenyl, and $C_{8-12}$ linear or branched, saturated or unsaturated alkyl. Additional examples of such R are:

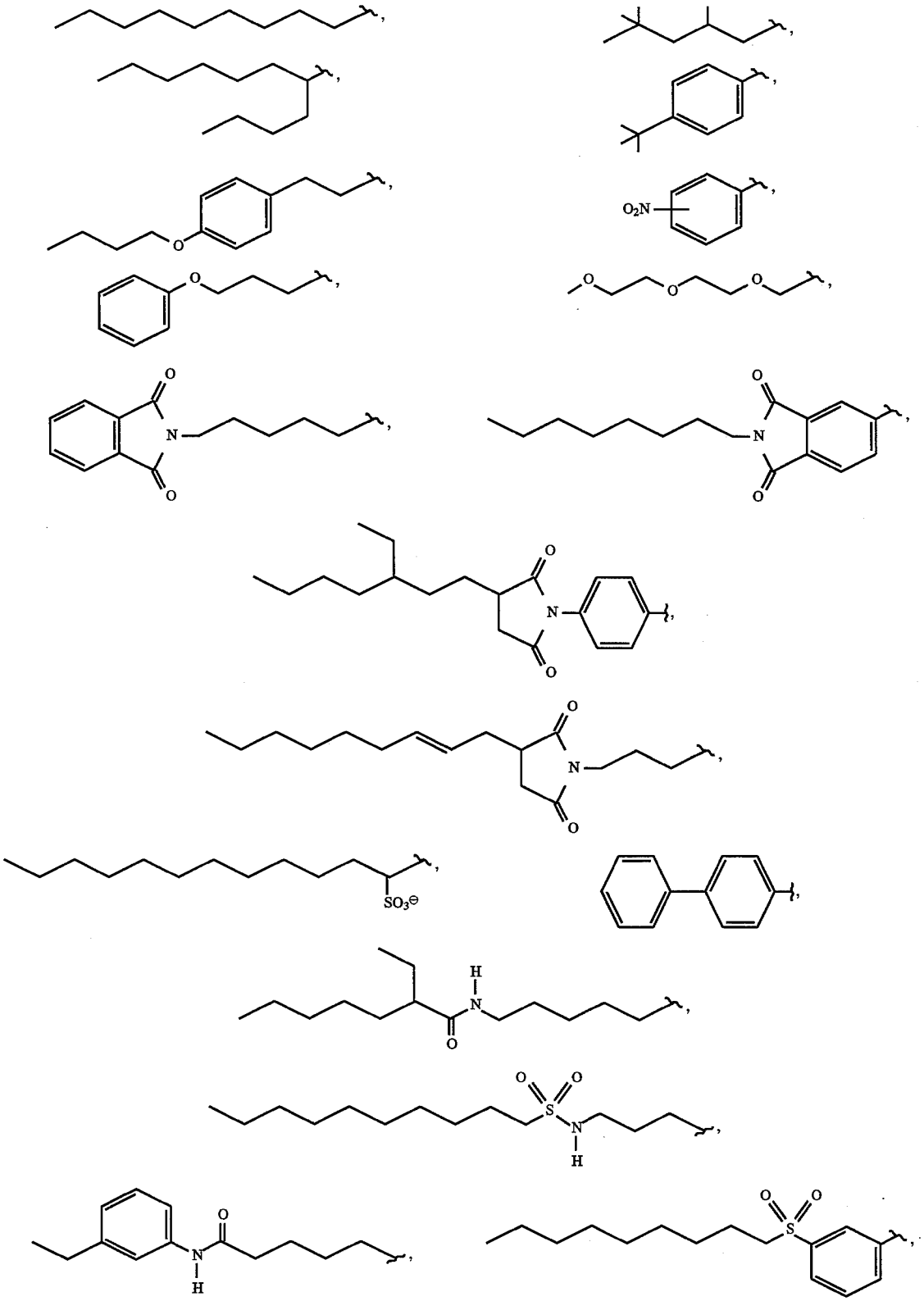

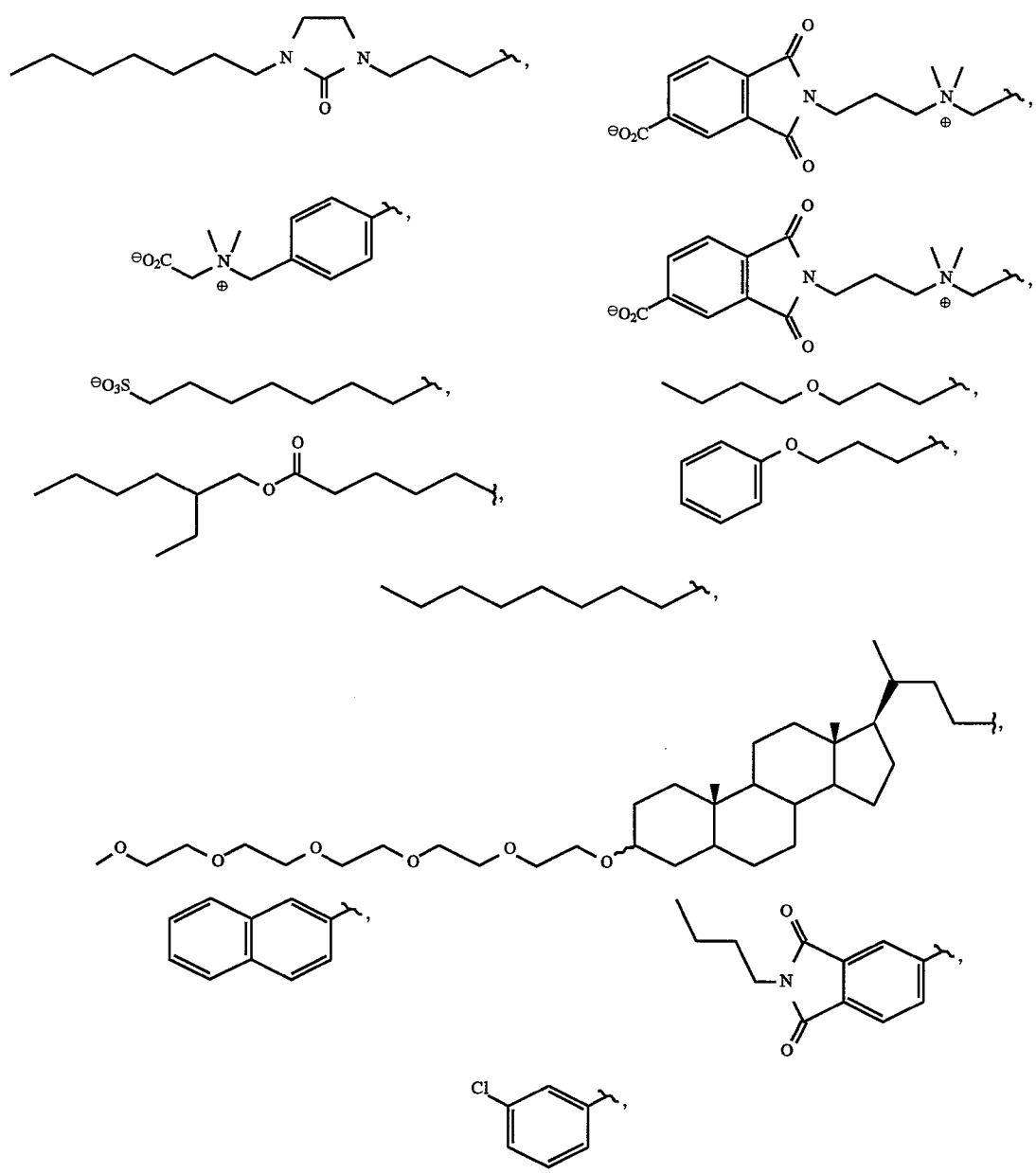

Note that in the R structures above, a common organic chemical structure drawing convention is used for brevity. In this convention,

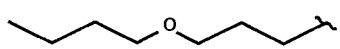

is equivalent to: $CH_3CH_2CH_2CH_2OCH_2CH_2CH_2$—. In general, R can be a difunctional radical, e.g.,

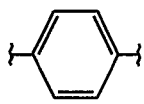

in which case the alpha-modified lactam bleach activators have the formula LC(O)RC(O)L' wherein the two alpha-modified lactam moieties, L and L', may be the same or different.

In general, for all preferred alpha-modified lactam bleach activators, R comprises more than two carbon atoms and encompasses both aromatic and aliphatic structures. The atom in R to which moiety —C(O)— of a lactam activator RC(O)L is bonded may be a heteroatom or a carbon atom, preferably a carbon atom:

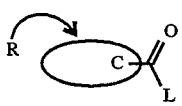

In preferred aromatic structures, R is connected to —C(O)— in said moiety RC(O)— through a carbon atom which forms part of an aromatic ring. Alpha-modified lactam bleach activators having such structure include those wherein R is phenyl or furyl. To illustrate this class more extensively, R can be a member selected from the group consisting of phenyl, 4-nitrophenyl, 3-chlorophenyl, 3,5-dinitrophenyl, 3,5-dichlorophenyl, 4-(alkylsulfonyl)phenyl, 2-furyl, 3-furyl, 5-nitro-2-furyl and 5-nitro-3-furyl; more preferably a member selected from the group consisting of phenyl, 3,5-dinitrophenyl, 3,5-dichlorophenyl, 4-(alkylsulfonyl)phenyl, 2-furyl, 3-furyl, 5-nitro-2-furyl and 5-nitro-3-furyl; more preferably still, R is a member selected from the group consisting of phenyl, 4-(alkylsulfonyl)phenyl, 2-furyl, 3-furyl, 5-nitro-2-furyl, 5-nitro-3-furyl and mixtures thereof.

In preferred embodiments R can be substantially free from chloro- or nitro-.

It will be recognized that R may be selected so as to confer surface-active character on the peracid which will result when the alpha-modified lactam bleach activator is perhydrolyzed, as in the case of R being a member selected from the group consisting of octyl, nonyl, 2,4,4-trimethylpentyl, 3-heptyl, and decyl. The resulting alpha-modified lactam bleach activators perform well, especially at higher wash pH's.

Excellent bleaching/cleaning can be achieved at lower wash pH's when R is electronegatively, electron-withdrawingly or aromatically substituted, as in phenyl, nitrophenyl, and numerous other R moieties identified hereinabove.

A preferred cleaning composition comprises alpha-modified lactam bleach activators wherein R and L are neutral moieties. More generally, R may be charged (including zwitterionics) or uncharged, as is the case for L; accordingly, suitable counter-ions as disclosed for L, supra, can be incorporated into the alpha-modified lactam bleach activators regardless of whether the charge originates in, or is localized in, R or L.

Indeed it will be clear from the disclosure that the alpha-modified lactam bleach activators for the inventive cleaning compositions can have widely varying structures, including structures such as:

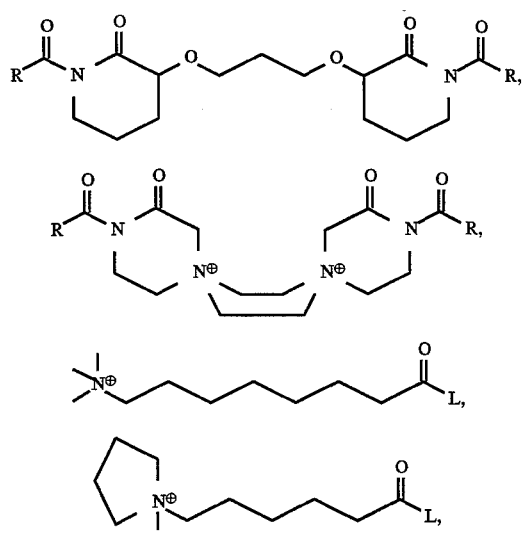

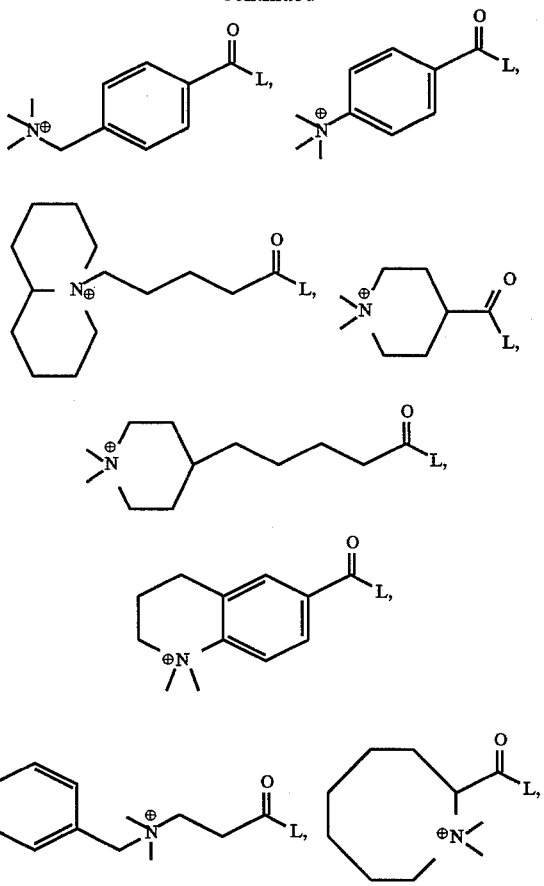

together with any of the foregoing R moieties incorporated into a compound of structure RC(O)L. In such compounds L is an alpha-modified lactam leaving-group as further defined and disclosed hereinafter. In general, the present compositions include activator structures in which a hetero-atom such as oxygen or nitrogen modifies the lactam ring. The hetero-atom will occupy the position denoted as "Z". Structures which involve the attachment of one or two non-hydrogen substituents (X,Y) exocyclically at the alpha ring position (marked by an asterisk in the structure (I) hereinabove) are also suitable. Five-membered through eight-membered lactam structures are encompassed.

When they are electrically charged as anions, cations, or polyionic compounds, alpha-modified lactam bleach activators herein may further include a charge-balancing number of compatible counterions. In acidic environments, protonation of trivalent nitrogen may occur when such nitrogen is present in the alpha-modified lactam bleach activator, forming "acid salts". These remain within the spirit and scope of the invention. On raising the pH (as in use), bleach activator structures such as those explicitly illustrated herein will rapidly be reformed.

Suitable anions herein are illustrated by the common water-soluble anions such as sulfate or any alternate compatible sulfur anion such as alkylsulfate or arylsulfonate. Various phosphate anions may likewise be used.

Suitable cations herein are illustrated by the common water-soluble cations such as sodium, potassium, tetra-alkylammonium and the like.

Anions and cations balancing the charge on any formally charged alpha-modified lactam bleach activator can equally well be derived from a surfactant, such as a $C_8$ alkyl sulfate, provided that such charge-balancing ion does not substantially inhibit the delivery of the alpha-modified lactam activators in use.

In a highly preferred bleach-additive, bleaching or cleaning composition, there are provided embodiments comprising from about 0.1% to about 10% of alpha-modified lactam bleach activator having the formula RC(O)L wherein R is a member selected from the group consisting of octyl, nonyl, 2,4,4-trimethylpentyl, 3-heptyl, decyl, phenyl, 3,5-dinitrophenyl, 3,5-dichlorophenyl, 4-(alkylsulfonyl)phenyl, 2-furyl, 3-furyl, 5-nitro-2-furyl and 5-nitro-3-furyl and L is a member selected from the group consisting of alpha-chlorocaprolactam, alpha-chlorovalerolactam, alpha, alpha-dichlorocaprolactam, alpha, alpha-dichlorovalerolactam, alpha-methoxy caprolactam, alpha-methoxyvalerolactam,

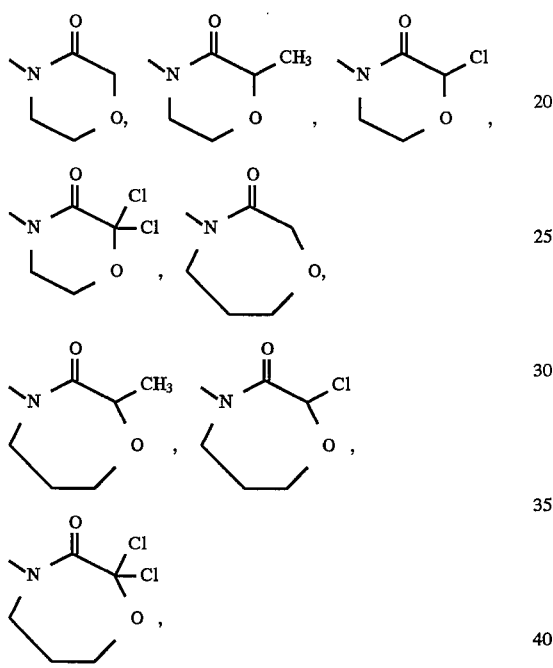

and mixtures thereof.

The foregoing compositions include novel cleaning, bleaching and bleach-additive compositions which are substantially free from hydrogen peroxide or hydrogen peroxide releasing sources; likewise encompassed are novel cleaning, bleaching and bleach-additive compositions comprising a source of hydrogen peroxide.

Whereas the present invention encompasses embodiments comprising selected alpha-modified bleach activators whether said compounds are themselves known for a different purpose or not, the invention is not limited to such compositions and also encompasses those alpha-modified lactam compounds which are new.

Included in the alpha-modified lactam compound embodiments are compounds having the formula (II):

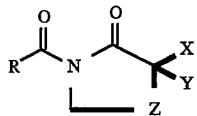 (II)

wherein R is a moiety comprising from about 4 to about 30 carbon atoms provided that R is different from —CH$_2$Ph and —(CH$_2$)$_8$CO$_2$H; Z is selected from:

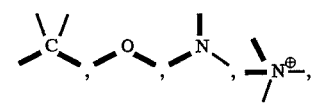

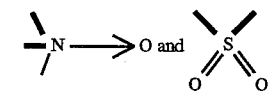

wherein any Z covalently connects through two valencies forming part of cyclic structure (II); and at least one of X and Y is selected from —Cl, —Br, —NO$_2$, —CN,

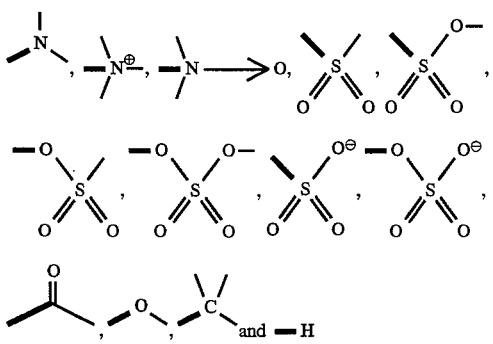

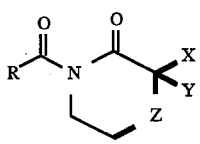

wherein one valency of any X and of any Y covalently connects said moiety X or Y to cyclic structure (II); and further provided that when Z is

at least one of X and Y is different from H.

Likewise encompassed are compounds having the formula (III):

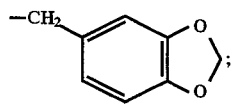 (III)

wherein R is a moiety comprising from about 4 to about 30 carbon atoms provided that R is different from —CH$_2$CH$_2$OCH$_2$Ph, —CH$_2$CH(CH$_3$)OCH$_2$Ph and

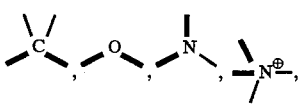

Z is selected from:

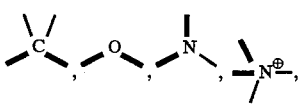

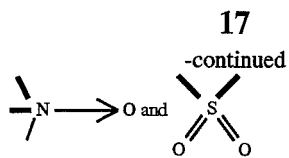

wherein any Z covalently connects through two valencies forming part of cyclic structure (III); at least one of X and Y is selected from —Cl, —Br, —NO$_2$, —CN,

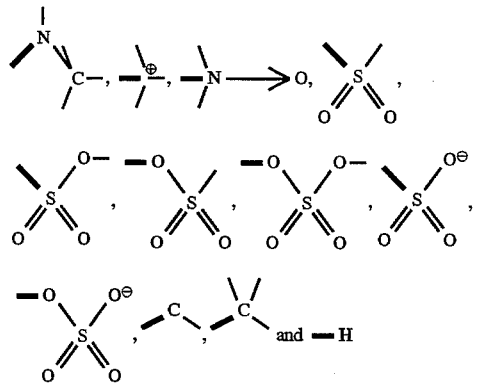

wherein one valency of any X and of any Y covalently connects said moiety X or Y to cyclic structure (III); provided that said moiety

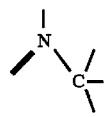

is different from

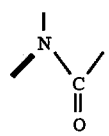

and said moiety

is different from

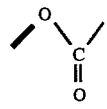

and further provided that when Z is

at least one of X and Y is different from H.

Also within the spirit and scope of the invention are compounds having the formula (IV):

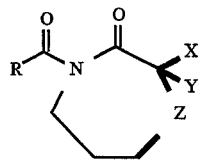

(IV)

wherein R is a moiety comprising from about 4 to about 30 carbon atoms; Z is selected from:

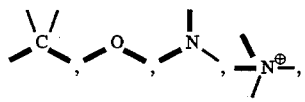

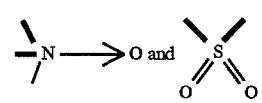

wherein any Z covalently connects through two valencies forming part of cyclic structure (IV); at least one of X and Y is selected from —Br, —NO$_2$, —CN,

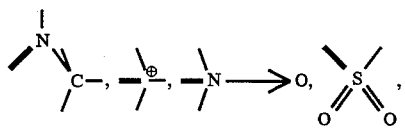

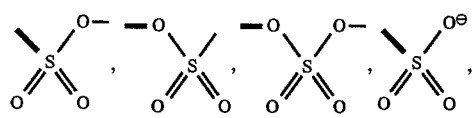

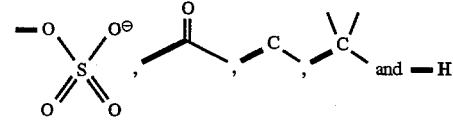

wherein one valency of any X and of any Y covalently connects said moiety X or Y to cyclic structure (IV); provided that said moiety

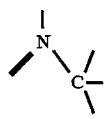

is different from

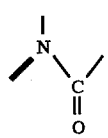

and further provided that when Z is

at least one of X and Y is different from H.

Measurable Characteristics

Alpha-modified lactam bleach activators herein have a number of measurable characteristics which permit the identification of additional suitable embodiments of the invention beyond those used in the nonlimiting illustrations hereinabove. There now follows a description of such embodiments followed by definition of the measurable characteristics used.

Thus, the invention encompasses a cleaning composition wherein said alpha-modified lactam bleach activator comprises a moiety RC(O)— which produces a peracid RC(O)—OOH on perhydrolysis; and said leaving-group, L covalently connects to said moiety RC(O)—; said alpha-modified lactam bleach activator having a perhydrolysis efficiency coefficient, of greater than about 0.10 and a ratio of $k_P/k_{CL}>1$ wherein $k_P$ is the rate constant for perhydrolysis of said alpha-modified lactam bleach activator and $k_{CL}$ is the rate constant for perhydrolysis under otherwise identical conditions of an unmodified lactam reference compound having the formula:

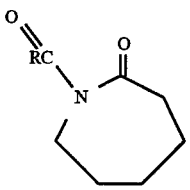

wherein RC(O)— is as defined in said moiety of said alpha-modified lactam bleach activator.

Also encompassed is a cleaning composition wherein said alpha-modified lactam bleach activator has a ratio $k_P/k_D \geq 2$, preferably $k_P/k_D \geq 5$, wherein $k_P$ is said rate constant for perhydrolysis and wherein $k_D$ is the rate constant for formation of a diacylperoxide from said alpha-modified bleach activator; a ratio $k_P/k_H \geq 1$, preferably $k_P/k_H \geq 2$, wherein $k_P$ is said rate constant for perhydrolysis and wherein $k_H$ is the rate constant for hydrolysis of said alpha-modified bleach activator, and said rate constant $k_H \leq 10 M^{-1} s^{-1}$.

Also encompassed is a cleaning composition wherein R is selected such that the difference in aqueous $pK_a$ between acetic acid and the carboxylic acid analog, RC(O)OH, of said peracid is at least 0.6 and L is selected such that its conjugate acid, HL, has an aqueous $pK_a$ in the range from greater than about 13 to less than about 17, and wherein RC(O)L has a low pH perhydrolysis efficiency coefficient of greater than about 0.20.

Test for High pH Perhydrolysis Efficiency (HPE)—Unless otherwise specifically indicated, use of the term "perhydrolysis efficiency" herein refers to high pH perhydrolysis efficiency, measured by a coefficient, as now set forth:

This method is applicable as a test for confirming the suitability of an alpha-modified lactam bleach activator as a preferred bleach activator in the cleaning compositions of the present invention. For the purposes of the test, it will be assumed the activator has the form RC(O)L (not intending to be limiting of any specific bleach activator structure herein). The test involves confirmation of the formation of peracid analyte $RC(O)O_2H$. The minimum standard for perhydrolysis efficiency (HPE) is a coefficient, as defined below, $\geq 0.10$ within 10 minutes when tested under the conditions specified.

Test Protocol for HPE—Distilled, deionized water (90 mL; pH adjusted to 10.3 with $Na_2CO_3$) is added to a 150 mL beaker and heated to $40°\pm1°$ C. Fifty (50) mg sodium percarbonate is added to the beaker and the mixture is stirred two minutes before a 10 mL solution containing 10 mg of alpha-modified lactam bleach activator (predissolved in 1 mL of a water miscible organic solvent (e.g., methanol or dimethylformamide) and brought to volume with pH 10.3 distilled, deionized water) is added. The initial time point is taken 1 minute thereafter. A second sample is removed at 10 minutes. Sample aliquots (2 mL) are examined via analytical HPLC for the quantitative determination of peracid $RC(O)O_2H$.

Sample aliquots are individually mixed with 2 mL of a pre-chilled 5° C. solution of acetonitrile/acetic acid (86/14) and placed in temperature controlled 5° C. autosampler for subsequent injection onto the HPLC column.

High performance liquid chromatography of the authentic peracid under a given set of conditions establishes the characteristic retention time ($t_R$) for the analyte. Conditions for the chromatography will vary depending on the peracid of interest and should be chosen so as to allow baseline separation of the peracid from other analytes. A standard calibration curve (peak area vs. concentration) is constructed using the peracid of interest. The analyte peak area of the 10 minute sample from the above described test is thereby converted to ppm peracid generated for determination of the quantity HPE. A bleach activator is considered acceptable when a value of the perhydrolysis efficiency coefficient, HPE=[(ppm of peracid generated)/(theoretical ppm peracid)] $\geq 0.10$ is achieved within ten minutes under the specified test conditions.

Test for Low pH Perhydrolysis Efficiency (LPE)

This method is applicable as a test for confirming the suitability of an alpha-modified lactam bleach activator as a preferred bleach activator in the cleaning compositions of the present invention. For the purposes of the test, it will be assumed the activator has the form RC(O)L (not intending to be limiting of any specific bleach activator structure herein). The test involves confirmation of the formation of peracid analyte $RC(O)O_2H$. The minimum standard for low pH perhydrolysis efficiency (LPE) is a coefficient, as defined below, $\geq 0.20$ within 10 minutes when tested under the conditions specified.

Test Protocol for LPE—Distilled, deionized water (495 mL; adjusted to pH 7.5 with $NaH_2PO_4$ and $Na_2HPO_4$) is added to a 1000 mL beaker and heated to $40°\pm1°$ C. Three hundred seventy-five (375) mg of 30% concentration hydrogen peroxide is added to the beaker and the mixture is stirred for two minutes before a 5 mL solution containing 100 mg of activator (predissolved in 5 mL of an organic solvent (e.g. methanol or dimethylformamide)) is added. The initial data point is taken 1 minute thereafter. A second sample is removed at 10 minutes. Sample aliquots (2 mL) are examined via analytical HPLC for the quantitative determination of peracid $RC(O)O_2H$.

Sample aliquots are individually mixed with 2 mL of a pre-chilled 5° C. solution of acetonitrile/acetic acid (86/14) and placed in temperature controlled 5° C. autosampler for subsequent injection onto the HPLC column.

High performance liquid chromatography of the authentic peracid under a given set of conditions establishes the characteristic retention time ($t_R$) for the analyte. Conditions for the chromatography will vary depending on the peracid of interest and should be chosen so as to allow baseline separation of the peracid from other analytes. A standard calibration curve (peak area vs. concentration) is constructed using the peracid of interest. The analyte peak area of the 10 minute sample from the above described test is thereby converted to ppm peracid generated for determination of the quantity LPE. A bleach activator is considered acceptable then a value of the low pH perhydrolysis efficiency coefficient, LPE=[(ppm of peracid generated)/(theoretica ppm peracid)]≧0.20s achieved within ten minutes under the specified test conditions.

pKa $pK_a$, Rate and Perhydrolysis Criticalities—In accordance with the present invention, there are provided certain preferred bleaching compositions wherein the bleach activators are required to respect criticalities of $pK_a$ and criticalities relating to rates of perhydrolysis, hydrolysis and diacylperoxide formation. Furthermore, perhydrolysis efficiency and low pH perhydrolysis efficiency are important in selecting certain preferred bleach activators. All of these criticalities will be better understood and appreciated in light of the following disclosure.

$pK_a$ Value—The acids in which organic chemists have traditionally been interested span a range, from the weakest acids to the strongest, of about 60 pK units. Because no single solvent is suitable over such a wide range, establishment of comprehensive scales of acidity necessitates the use of several different solvents. Ideally, one might hope to construct a universal acidity scale by relating results obtained in different solvent systems to each other. Primarily because solute-solvent interactions affect acid-base equilibria differently in different solvents, it has not proven possible to establish such a scale.

Water is taken as the standard solvent for establishing an acidity scale. It is convenient, has a high dielectric constant, and is effective at solvating ions. Equilibrium acidities of a host of compounds (e.g., carboxylic acids and phenols) have been determined in water. Compilations of pK data may be found in Perrin, D. D. "Dissociation Constants of Organic Bases in Aqueous Solution"; Butterworths: London, 1965 and Supplement, 1973; Serjeant, E. P.; Dempsey, B. "Ionisation Constants of Organic Acids in Aqueous Solution"; 2nd ed., Pergammon Press: Oxford, 1979. Experimental methods for determining $pK_a$ values are described in the original papers. The $pK_a$ values that fall between 2 and 10 can be used with a great deal of confidence; however, the further removed values are from this range, the greater the degree of skepticism with which they must be viewed.

For acids too strong to be investigated in water solution, more acidic media such as acetic acid or mixtures of water with perchloric or sulfuric acid are commonly employed; for acids too weak to be examined in water, solvents such as liquid ammonia, cyclohexylamine and dimethylsulfoxide have been used. The Hammett $H_o$ acidity function has allowed the aqueous acidity scale, which has a practical $pK_a$ range of about 0–12, to be extended into the region of negative $pK_a$ values by about the same range. The use of $H_-$ acidity functions that employ strong bases and cosolvents has similarly extended the range upward by about 12 $pK_a$ units.

Some preferred embodiments of the present invention involve the use of leaving groups the conjugate acids of which are considered to be weak; they possess aqueous $pK_a$ values greater than about 13. To establish only that a given compound has an aqueous $pK_a$ above about 13 is straightforward. As noted above, values much above this are difficult to measure with confidence without resorting to the use of an acidity function. The measurement of the acidity of weak acids using the $H_-$ method, which has the advantage of an aqueous standard state, is suitable for determining if the conjugate acid, HL, of leaving group, L, has an aqueous pKa of greater than about 13 to less than about 17.

Definitions of $k_H$, $k_P$, $k_{CL}$, and $k_D$—In the expressions given below, the choice of whether to use the concentration of a nucleophile or of its anion in the rate equation was made as a matter of convenience. One skilled in the art will realize that measurement of solution pH provides a convenient means of directly measuring the concentration of hydroxide ions present. One skilled in the art will further recognize that use of the total concentrations of hydrogen peroxide and peracid provide the most convenient means to determine the rate constants $k_P$ and $k_D$.

The terms, such as RC(O)L, used in the following definitions and in the conditions for the determination of $k_H$, $k_P$ and $k_D$, are illustrative of a general bleach activator structure and are not limiting to any specific bleach activator structure herein.

Definition of $k_H$

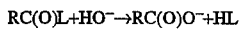

The rate of the reaction shown above is given by

Rate=$k_H$[RC(O)L][HO$^-$]

The rate constant for hydrolysis of bleach activator ($k_H$) is the second order rate constant for the bimolecular reaction between bleach activator and hydroxide anion as determined under the conditions specified below.

Definition of $k_P$

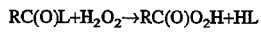

The rate of the reaction shown above is given by

Rate=$k_P$[RC(O)L][H$_2$O$_2$]$_T$ where [H$_2$O$_2$]$_T$ represents the total concentration of hydrogen peroxide and is equal to [H$_2$O$_2$]+[HO$_2^-$].

The rate constant for perhydrolysis of bleach activator ($k_P$) is the second order rate constant for the bimolecular reaction between bleach activator and hydrogen peroxide as determined under the conditions specified below.

Definition of $k_{CL}$

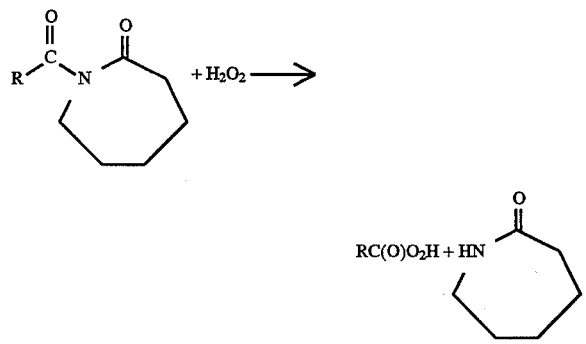

The rate of the reaction shown above is given by

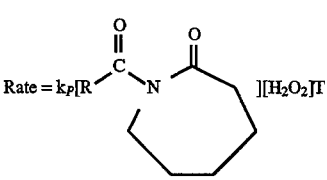

where [H$_2$O$_2$]$_T$ represents the total concentration of hydrogen peroxide and is equal to [H$_2$O$_2$]+[HO$_2^-$].

The rate constant for perhydrolysis of a reference bleach activator RC(O)L wherein the leaving group L is caprolactam ($k_{CL}$) is the second order rate constant for the bimolecular reaction between said reference bleach activator and hydrogen peroxide as determined under the conditions specified below for the determination of the rate constant $k_P$.

Definition of $k_D$ $$RC(O)L + RC(O)O_2H \rightarrow RC(O)O_2C(O)R + HL$$

The rate of the reaction shown above is given by $$\text{Rate} = k_D[RC(O)L][RC(O)O_2H]_T$$

where $[RC(O)O_2H]_T$ represents the total concentration of peracid and is equal to $[RC(O)O_2H]+[RC(O)O_2^-]$.

The rate constant for the formation of a diacylperoxide from the bleach activator ($k_D$), the second order rate constant for the bimolecular reaction between bleach activator and peracid anion, is calculated from the above defined $k_{D'}$. The value for $k_{D'}$ is determined under the conditions specified below.

Definition of Perhydrolysis Selectivity Coefficient—Perhydrolysis selectivity coefficient is defined as the ratio $k_P/k_D$ wherein $k_P$ and $k_D$ are as defined above.

Conditions for the Determination of Rate Constants:

Hydrolysis—A set of experiments is completed to measure the rate of hydrolysis of a bleach activator RC(O)L in aqueous solution at total ionic strength of 1M as adjusted by addition of NaCl. The temperature is maintained at 35.0°±0.1° C. and the solution is buffered with $NaHCO_3 + Na_2CO_3$. A solution of the activator ([RC(O)L]=0.5 mM) is reacted with varying concentrations of NaOH under stopped-flow conditions and the rate of reaction is monitored optically. Reactions are run under pseudo first-order conditions to determine the bimolecular rate constant for hydrolysis of bleach activator ($k_H$). Each kinetic run is repeated at least five times with about eight different concentrations of hydroxide anions. All kinetic traces give satisfactory fits to a first-order kinetic rate law and a plot of the observed first-order rate constant versus concentration of hydroxide anion is linear over the region investigated. The slope of this line is the derived second order rate constant $k_H$.

Perhydrolysis—A set of experiments is completed to measure the rate of perhydrolysis of a bleach activator RC(O)L in aqueous solution at pH=10.0 with constant ionic strength of 1M as adjusted by addition of NaCl. The temperature is maintained at 35.0°±0.1° C. and the solution is buffered with $NaHCO_3 + Na_2CO_3$. A solution of the activator ([RC(O)L]=0.5 mM) is reacted with varying concentrations of sodium perborate under stopped-flow conditions and the rate of reaction is monitored optically. Reactions are run under pseudo first-order conditions in order to determine the bimolecular rate constant for perhydrolysis of bleach activator ($k_P$). Each kinetic run is repeated at least five times with about eight different concentrations of sodium perborate. All kinetic traces give satisfactory fits to a first-order kinetic rate law and a plot of the observed first-order rate constant versus total concentration of hydrogen peroxide is linear over the region investigated. The slope of this line is the derived second order rate constant $k_P$. One skilled in the art recognizes that this rate constant is distinct from, but related to, the second order rate constant for the reaction of a bleach activator with the anion of hydrogen peroxide ($k_{nuc}$). The relationship of these rate constants is given by the following equation:

$$k_{nuc} = k_P\{(K_a + [H^+])/K_a\}$$

where $K_a$ is the acid dissociation constant for hydrogen peroxide.

Formation of diacylperoxide—A set of experiments is completed to measure the rate of formation of a diacylperoxide $RC(O)O_2C(O)R$ from a bleach activator RC(O)L in aqueous solution at pH=10.0 with constant ionic strength of 1M as adjusted by addition of NaCl. The temperature is maintained at 35.0°±0.1° C. and the solution is buffered with $NaHCO_3 + Na_2CO_3$. A solution of the activator ([RC(O)L]= 0.5 mM) is reacted with varying concentrations of peracid under stopped-flow conditions and the rate of reaction is monitored optically. Reactions are run under pseudo first-order conditions in order to determine the bimolecular rate constant $k_{D'}$. Each kinetic run is repeated at least five times with about eight different concentrations of peracid anion. All kinetic traces give satisfactory fits to a first-order kinetic rate law and a plot of the observed first-order rate constant versus total concentration of peracid is linear over the region investigated. The slope of this line is the derived second order rate constant $k_{D'}$. The bimolecular rate constant for the formation of a diacylperoxide from peracid anion ($k_D$) is calculated according to $$k_D = k_{D'}\{(K_a + [H^+])/K_a\}$$

where $K_a$ is the acid dissociation constant for the peracid $RC(O)O_2H$. One skilled in the art will realize that the $pK_a$ values for peracids fall into a rather narrow range from about 7 to about 8.5 and that at pH=10.0, when $K_a \geq$ about $10^{-8}$, $\{(K_a+[H^+])/K_a\} \cong 1$ and $k_D \cong k_{D'}$.

Determination of $k_H$, $k_P$, $k_{CL}$ and $k_D$ when Bleach Activator has formula $R(C(O)L)_x$ wherein $x>1$. The present invention comprises bleach activator embodiments wherein there are single or multiple C(O)L groups. When only a single —C(O)L moiety is present, measurement of $k_H$, $k_P$, $k_{CL}$ and $k_D$ is accomplished straightforwardly as described hereinabove. When the bleach activator comprises multiple —C(O)L groups, those skilled in the art will realize that the determination of $k_H$, $k_P$, $k_{CL}$ and $k_D$ for such bleach activators is best accomplished through the use of model compounds. "Model compounds", herein designated as MC(O) L, are chemical compounds identified purely for purposes of simplifying testing and measurement, and are not required to lie within the instant invention (though they may in certain instances do so). The formula of model compounds is generally arrived at by replacing all but one of the —C(O)L moieties in any multiple —C(O)L— containing bleach activator with methyl or H.

A number of different cases are identified, depending on the precise formula of the bleach activator:

For bleach activators of formula $R(C(O)L)_x$ wherein $x>1$:

Case (i) When R is symmetric and all C(O)L groups are identical, a single model compound is required.

Case (ii) When R is symmetric and all C(O)L groups are not identical, x model compounds are needed.

Case (iii) When R is asymmetric, x model compounds are needed regardless of whether or not all C(O)L groups are identical.

The choice of suitable model compounds is nonlimitingly illustrated as follows. Examples of each case described above are illustrated below for both neutral and charged R moieties.

Case (i); neutral R moiety
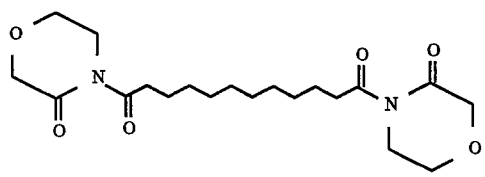
A model compound for the above is:
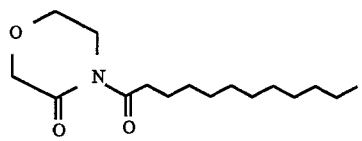
Case (i); charged R moiety
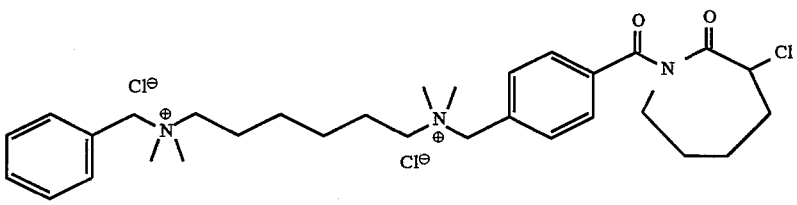
A model compound for the above is:
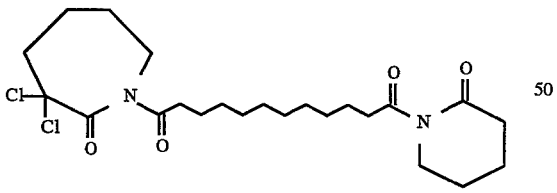
Case (ii); neutral R moiety
Model compounds for the above are:
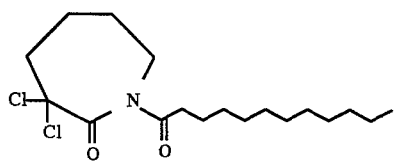
and
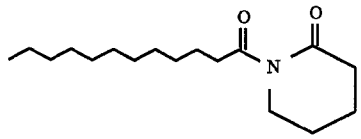
Case (ii); charged R moiety
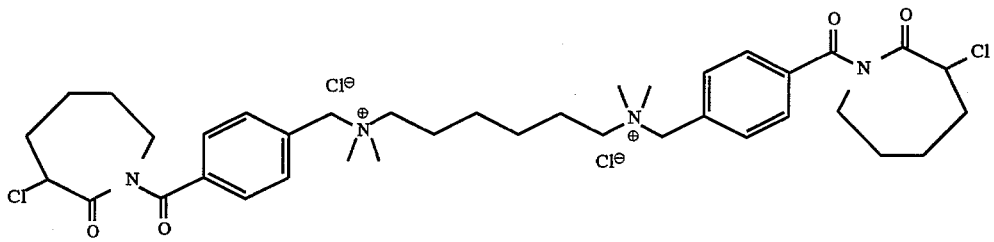

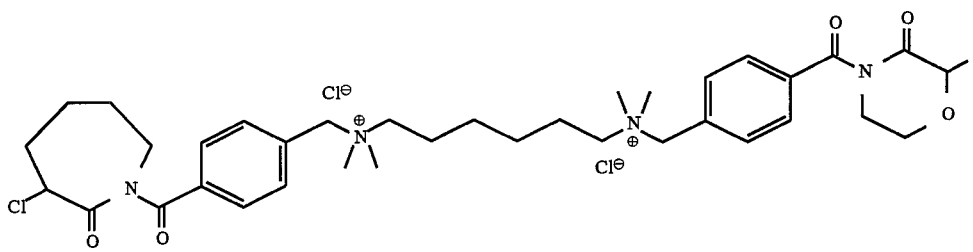
Two model compounds for the above are:
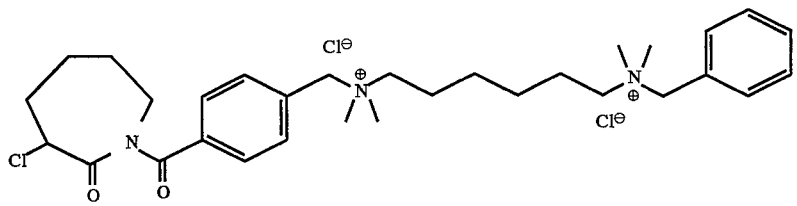
and
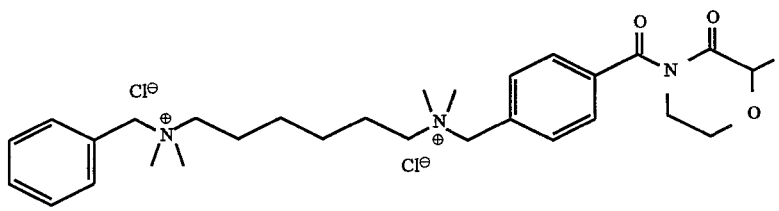
Case (iii); neutral R moiety
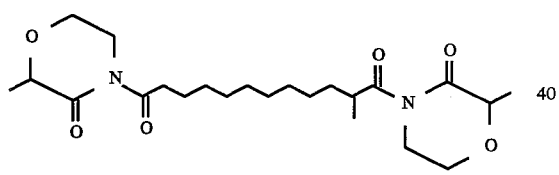
Model compounds for the above are:
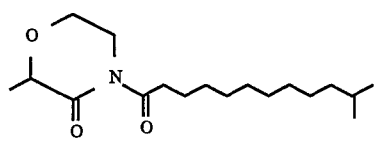
and
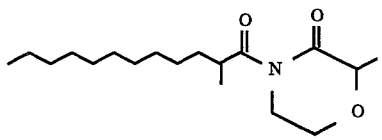
Case (iii); charged R moiety
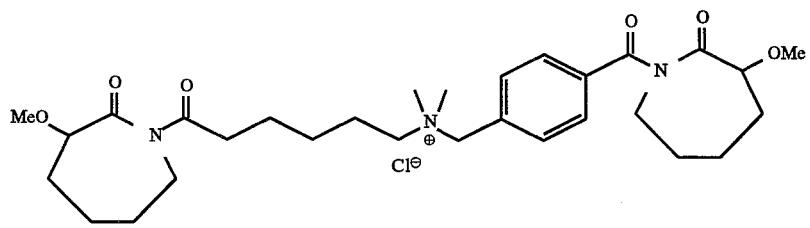

Model compounds for the above are:

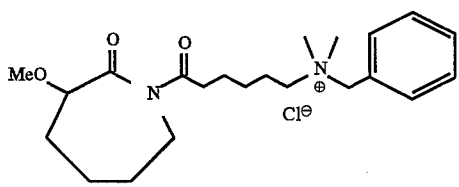

and

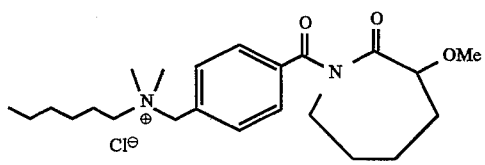

The above examples are given by way of illustration. One skilled in the art will realize that if the connection between any two —C(O)L is conjugated, any electronic effect of one —C(O)L on the kinetics of the other must be suitably accounted for in the model compounds chosen.

When model compounds have been selected for a multiple —C(O)L— containing bleach activator, $k_H$, $k_P$ and $k_D$ are measured for each model compound as described hereinabove. The bleach activator corresponding to the set of model compounds is considered to conform with the $k_P/k_H$, $k_P/k_D$ and $k_H$ criticalities of the invention provided that at least one model compound MC(O)L, wherein L is a novel leaving group of the instant invention, meets the specified $k_P/k_H$, $k_P/k_D$ and $k_H$ criticalities. Said model compound must also satisfy the requirement that $k_P$ is greater than $k_{CL}$, wherein $k_{CL}$ is the rate constant for perhydrolysis under otherwise identical conditions of a reference bleach activator having the formula:

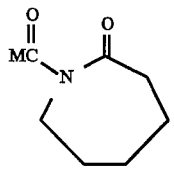

wherein MC(O)— is as defined in said moiety of said model compound.

Hydrogen Peroxide Source: Types, Levels, and Modes of Use

A source of hydrogen peroxide herein is any convenient compound or mixture which under consumer use conditions provides an effective amount of hydrogen peroxide. Levels may vary widely and are typically from about 0.5% to about 70%, more typically from about 0.5% to about 25%, by weight of the cleaning or bleaching compositions herein.

The source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Mixtures of any convenient hydrogen peroxide sources can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources such as FMC, Solvay and Tokai Denka.

Other Ingredients for Cleaning Compositions

Fully-formulated laundry and automatic dishwashing compositions typically will also comprise other adjunct ingredients to improve or modify performance. Typical, non-limiting examples of such ingredients are disclosed hereinafter for the convenience of the formulator.

Adjunct Ingredients

Bleach catalysts—If desired, cleaning compositions herein may additionally incorporate a catalyst or accelerator to further improve bleaching. Any suitable bleach catalyst can be used. Typical bleach catalysts comprise a transition-metal complex, often one wherein the metal co-ordinating ligands are quite resistant to labilization. Such catalyst compounds often have features of naturally occurring compounds but are principally provided synthetically and include, for example, the manganese-based catalysts disclosed in U.S. Pat. Nos. 5,246,621, 5,244,594; 5,194,416; 5,114,606; and European Pat. App. Pub. Nos. 549,271A1, 549,272A1, 544,440A2, and 544,490A1; preferred examples of these catalysts include $Mn^{IV}_2(u-O)_3(1,4,7$-trimethyl-1,4,7-triazacyclononane$)_2$-$(PF_6)_2$, $Mn^{III}_2(u-O)_1(u$-OAc$)_2(1,4,7$-trimethyl-1,4,7-triazacyclononane$)_2(ClO_4)_2$, $Mn^{IV}_4(u-O)_6(1,4,7$-triazacyclononane$)_4(ClO_4)_4$, $Mn^{III}$-$Mn^{IV}_4(u-O)_1(u$-OAc$)_2$-$(1,4,7$-trimethyl-1,4,7-triazacyclononane$)_2$-$(ClO_4)_3$, $Mn^{IV}(1,4,7$-trimethyl-1,4,7-triazacyclononane$)$-$(OCH_3)_3(PF_6)$, and mixtures thereof; though alternate metal-co-ordinating ligands as well as mononuclear complexes are also possible and monometallic as well as di- and polymetallic complexes, and complexes of alternate metals such as iron are all within the present scope. Other metal-based bleach catalysts include those disclosed in U.S. Pat. Nos. 4,430,243 and U.S. Pat. No. 5,114,611. The use of manganese with various complex ligands to enhance bleaching is also reported in the following U.S. Pat. Nos.: 4,728,455; 5,284,944; 5,246,612; 5,256,779; 5,280,117; 5,274,147; 5,153,161; and 5,227,084.

Said manganese can be precomplexed with ethylenediaminedisuccinate or separately added, for example as a sulfate salt, with ethylenediaminedisuccinate. (See U.S. patent application Ser. No. 08/210,186, filed Mar. 17, 1994.) Other preferred transition metals in said transition-metal-containing bleach catalysts include iron or copper.

Remarkably, preferred embodiments of the present invention in which the wash pH is in the range from about 6.5 to about 9.5 and there is present one of the above-indicated selected alpha-modified bleach activators in combination with one of the above-indicated bleach catalysts, secure a particularly superior bleaching effect as compared with otherwise identical compositions in which conventional bleach activators such as tetraacetylethylenediamine are used in place of the essential bleach activator.

As a practical matter, and not by way of limitation, the bleaching compositions and processes herein can be adjusted to provide on the order of at least one part per ten million of the active bleach catalyst species in the aqueous washing liquor, and will preferably provide from about 0.1 ppm to about 700 ppm, more preferably from about 1 ppm to about 50 ppm, of the catalyst species in the laundry liquor.

Conventional Bleach Activators—"Conventional bleach activators" herein are any bleach activators which do not respect the above-identified provisions given in connection with the essential, alpha-modified lactam bleach activators. Numerous conventional bleach activators are known and are optionally included in the instant bleaching/cleaning compositions and/or detergent additives. Various nonlimiting examples of such activators are disclosed in U.S. Pat. No. 4,915,854, issued Apr. 10, 1990 to Mao et al, and U.S. Pat. No. 4,412,934. The nonanoyloxybenzene sulfonate (NOBS) and tetraacetylethylenediamine (TAED) activators are typical, and mixtures thereof or with the instant alpha-modified lactam bleach activators can also be used. See also U.S. Pat. No. 4,634,551 for other typical conventional bleach activators. Also known are amido-derived bleach activators of the formulae: $R^1N(R^5)C(O)R^2C(O)L$ or $R^1C(O)N(R^5)R^2C(O)L$ wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group other than an alpha-modified lactam. Further illustration of optional, conventional bleach activators of the above formulae include (6-octanamidocaproyl)oxybenzenesulfonate, (6-nonanamidocaproyl)oxybenzenesulfonate, (6-decanamidocaproyl)oxybenzenesulfonate, and mixtures thereof as described in U.S. Pat. No. 4,634,551. Another class of conventional bleach activators comprises the benzoxazin-type activators disclosed by Hodge et al in U.S. Pat. No. 4,966,723, issued Oct. 30, 1990. Still another class of conventional bleach activators includes those acyl lactam activators which do not provide the benefits of, nor have the criticalities of the alpha-modified lactam bleach activators described herein. Examples of optional lactam activators which are not alpha-modified include octanoyl caprolactam, 3,5,5-trimethylhexanoyl caprolactam, nonanoyl caprolactam, decanoyl caprolactam, undecenoyl caprolactam, octanoyl valerolactam, decanoyl valerolactam, undecenoyl valerolactam, nonanoyl valerolactam, 3,5,5-trimethylhexanoyl valerolactam and mixtures thereof.

Bleaching agents other than hydrogen peroxide sources are also known in the art and can be utilized herein as adjunct ingredients. One type of non-oxygen bleaching agent of particular interest includes photoactivated bleaching agents such as the sulfonated zinc and/or aluminum phthalocyanines. See U.S. Pat. No. 4,033,718, issued Jul. 5, 1977 to Holcombe et al. If used, detergent compositions will typically contain from about 0.025% to about 1.25%, by weight, of such bleaches, especially sulfonated zinc phthalocyanine.

Organic Peroxides, especially Diacyl Peroxides—are extensively illustrated in Kirk Othmer, Encyclopedia of Chemical Technology, Vol. 17, John Wiley and Sons, 1982 at pages 27–90 and especially at pages 63–72, all incorporated herein by reference. Suitable organic peroxides, especially diacyl peroxides, are further illustrated in "Initiators for Polymer Production", Akzo Chemicals Inc., Product Catalog, Bulletin No. 88–57, incorporated by reference. Preferred diacyl peroxides herein whether in pure or formulated form for granule, powder or tablet forms of the bleaching compositions constitute solids at 25° C., e.g., CADET® BPO 78 powder form of dibenzoyl peroxide, from Akzo. Highly preferred organic peroxides, particularly the diacyl peroxides, for such bleaching compositions have melting points above 40° C., preferably above 50° C. Additionally, preferred are the organic peroxides with SADT's (as defined in the foregoing Akzo publication) of 35° C. or higher, more preferably 70° C. or higher. Nonlimiting examples of diacyl peroxides useful herein include dibenzoyl peroxide, lauroyl peroxide, and dicumyl peroxide. Dibenzoyl peroxide is preferred. In some instances, diacyl peroxides are available in the trade which contain oily substances such as dioctyl phthalate. In general, particularly for automatic dishwashing applications, it is preferred, if they are to be used at all, to employ diacyl peroxides which are substantially free from oily phthalates since these can form smears on dishes and glassware. Preferred cleaning compositions herein, for example granular laundry detergents for use under European conditions as well as certain granular or liquid-form automatic dishwashing detergents, include, but are not limited to, compositions into which no preformed diacylperoxide has deliberately been added.

Quaternary Substituted Bleach Activators—The present compositions can optionally further comprise conventional, known quaternary substituted bleach activators (QSBA). QSBA's are further illustrated in U.S. Pat. No. 4,539,130, Sep. 3, 1985 and U.S. Pat. No. 4,283,301. British Pat. 1,382,594, published Feb. 5, 1975, discloses a class of QSBA's optionally suitable for use herein. U.S. Pat. No. 4,818,426 issued Apr. 4, 1989 discloses another class of QSBA's. Also see U.S. Pat. No. 5,093,022 issued Mar. 3, 1992 and U.S. Pat. No. 4,904,406, issued Feb. 27, 1990. Additionally, QSBA's are described in EP 552,812 A1 published Jul. 28, 1993, and in EP 540,090 A2, published May 5, 1993.

Detersive Surfactants—Surfactants are useful herein for their usual cleaning power and may be included in preferred embodiments of the instant cleaning and/or bleaching compositions at the usual detergent-useful levels. Depending on the precise application, such compositions are better than the surfactant-free counterparts for overall cleaning and bleaching performance and may be synergistic. In general, bleach-stable detersive surfactants are preferred: for example, for long-term storage stability, particularly of liquid-form cleaning compositions comprising bleach, it is preferable to use detersive surfactants in which the total content of bleach-reactive unsaturated surface-active material or other impurity components is minimized.

Nonlimiting examples of surfactants useful herein include the conventional $C_{11}$–$C_{18}$ alkylbenzene sulfonates ("LAS") and primary, branched-chain and random $C_{10}$–$C_{20}$ alkyl sulfates ("AS"); the $C_{10}$–$C_{18}$ secondary alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium; unsaturated sulfates such as oleyl sulfate; the $C_{10}$–$C_{18}$ alkyl alkoxy sulfates ("$AE_xS$") especially those wherein x is from 1 to about 7; $C_{10}$–$C_{18}$ alkyl alkoxy carboxylates (especially the EO 1–5 ethoxycarboxylates); the $C_{10}$–$C_{18}$ glycerol ethers; the $C_{10}$–$C_{18}$ alkyl polyglycosides and their corresponding sulfated polyglycosides; and $C_{12}$–$C_{18}$ alpha-sulfonated fatty acid esters. Detersive surfactants may be mixed in varying proportions for improved surfactancy as is well-known in the art. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxylate/propoxylates), $C_{12}$–$C_{18}$ betaines and sulfobetaines ("sultaines"), $C_{10}$–$C_{18}$ amine oxides, and the like, can also be included in the cleaning compositions, The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be employed. If high sudsing is desired, the branched-chain $C_{10}$–$C_{16}$ soaps may be used. Mixtures of anionic and nonionic surfactants are especially useful. Automatic dishwashing compositions typically employ low sudsing surfactants, such as the mixed ethyleneoxy/propyleneoxy nonionics. Other conventional useful surfactants are listed in standard texts.

Builders—Detergent builders can optionally be included in the compositions herein to assist in controlling mineral hardness. Inorganic as well as organic builders can be used. Builders are typically used in automatic dishwashing and fabric laundering compositions to assist in the removal of particulate soils.

The level of builder can vary widely depending upon the end use of the composition and its desired physical form. When present, the compositions will typically comprise at least about 1% builder. High performance compositions typically comprise from about 10% to about 80%, more typically from about 15% to about 50% by weight, of the detergent builder. Lower or higher levels of builder, however, are not excluded.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulfates, and aluminosilicates. However, non-phosphate builders are required in some locales. Compositions herein function surprisingly well even in the presence of "weak" builders (as compared with phosphates) such as citrate, or in the so-called "underbuilt" situation that may occur with zeolite or layered silicate builders. See U.S. Pat. No. 4,605,509 for examples of preferred aluminosilicates.

Examples of silicate builders are the alkali metal silicates, particularly those having a $SiO_2$:$Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6® is a crystalline layered silicate marketed by Hoechst (commonly abbreviated herein as "SKS-6"). Unlike zeolite builders, the Na SKS-6 silicate builder does not contain aluminum. NaSKS-6 is the $\delta$-$Na_2SiO_5$ form of layered silicate and can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the $\alpha$-, $\beta$- and $\gamma$-forms. Other silicates may also be useful, such as for example magnesium silicate, which can serve as a crispening agent in granular formulations, as a stabilizing agent for oxygen bleaches, and as a component of suds control systems.

Silicates useful in automatic dishwashing (ADD) applications include granular hydrous 2-ratio silicates such as BRITESIL® H20 from PQ Corp., and the commonly sourced BRITESIL® H24 though liquid grades of various silicates can be used when the ADD composition has liquid form. Within safe limits, sodium metasilicate or sodium hydroxide alone or in combination with other silicates may be used in an ADD context to boost wash pH to a desired level.

Examples of carbonate builders are the alkaline earth and alkali metal carbonates as disclosed in German Patent Application No. 2,321,001 published on Nov. 15, 1973. Various grades and types of sodium carbonate and sodium sesquicarbonate may be used, certain of which are particularly useful as carriers for other ingredients, especially detersive surfactants.

Aluminosilicate builders may be used in the present compositions. Aluminosilicate builders are of great importance in most currently marketed heavy duty granular detergent compositions, and can also be a significant builder ingredient in liquid detergent formulations. Aluminosilicate builders include those having the empirical formula: $[M_z(zAlO_2)_y] \cdot xH_2O$ wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula: $Na_{12}[(AlO_2)_{12}(SiO_2)_{12}] \cdot xH_2O$ wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter. Individual particles can desirably be even smaller than 0.1 micron to further assist kinetics of exchange through maximization of surface area. High surface area also increases utility of aluminosilicates as adsorbents for surfactants, especially in granular compositions. Aggregates of silicate or aluminosilicate particles may be useful, a single aggregate having dimensions tailored to minimie segregation in granular compositions, while the aggregate particle remains dispersible to submicron individual particles during the wash. As with other builders such as carbonates, it may be desirable to use zeolites in any physical or morphological form adapted to promote surfactant carrier function, and appropriate particle sizes may be freely selected by the formulator.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt or "overbased". When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5- trihydroxybenzene-2,4,6-trisulfonic acid, and carboxymethyloxysuccinic acid, the various alkali metal, ammonium and substituted ammonium salts of polyacetic acids such as ethylenediaminetetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty laundry detergent formulations due to their availability from renewable resources and their biodegradability. Citrates can also be used in combination with zeolite and/or layered silicate builders. Oxydisuccinates are also especially useful in such compositions and combinations.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing in laundry compositions, which may need to be be taken into account by the formulator. Fatty acids or their salts may be undesirable in Automatic Dishwashing (ADD) embodiments in situations wherein soap scums can form and be deposited on dishware.

Where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used though such materials are more commonly used in a low-level mode as chelants or stabilizers.

Chelating Agents—The compositions herein may also optionally contain one or more transition-metal selective sequestrants or "chelating agents", e.g., iron and/or copper and/or manganese chelating agents, provided that such materials are compatible or suitably formulated. Chelating agents suitable for use herein can be selected from the group consisting of aminocarboxylates, phosphonates (especially the aminophosphonates), polyfunctionally-substituted aromatic chelating agents, and mixtures thereof. Without intending to be bound by theory, it is believed that the benefit of these materials is due in part to their exceptional ability to remove iron, copper and manganese ions from washing solutions by formation of soluble chelates; other benefits include inorganic film prevention or scale inhibition. Commercial chelating agents for use herein include the DEQUEST® series, and chelants from Monsanto, DuPont, and Nalco, Inc.

Aminocarboxylates useful as optional chelating agents are further illustrated by ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts thereof.

In general, chelant mixtures may be used for a combination of functions, such as multiple transition-metal control, long-term product stabilization, and/or control of precipitated transition metal oxides and/or hydroxides.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A highly preferred biodegradable chelator for use herein is ethylenediamine disuccinate ("EDDS"), especially (but not limited to) the [S,S] isomer as described in U.S. Pat. No. 4,704,233, Nov. 3, 1987, to Hartman and Perkins. The trisodium salt is preferred though other forms, such as magnesium salts, may also be useful.

Aminophosphonates are also suitable for use as chelating agents in the compositions of the invention when at least low levels of total phosphorus are permitted in detergent compositions, and include the ethylenediaminetetrakis (methylenephosphonates) and the diethylenetriaminepentakis (methylene phosphonates). Preferably, these aminophosphonates do not contain alkyl or alkenyl groups with more than about 6 carbon atoms.

If utilized, chelating agents or transition-metal-selective sequestrants will preferably comprise from about 0.001% to about 10%, more preferably from about 0.05% to about 1% by weight of the compositions herein.

Enzymes—Enzymes can be included in the instant compositions for a wide variety of fabric laundering or other cleaning purposes, including removal of protein-based, carbohydrate-based, or triglyceride-based stains, for example, and for the prevention of refugee dye transfer, and for fabric restoration. The enzymes to be incorporated include proteases, amylases, lipases, cellulases, and peroxidases, as well as mixtures thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders, etc. In this respect bacterial or fungal enzymes are preferred, such as bacterial amylases and proteases, and fungal cellulases.

Enzymes are normally incorporated at levels sufficient to provide up to about 5 mg by weight, more typically about 0.01 mg to about 3 mg, of active enzyme per gram of the composition. Stated otherwise, the compositions herein will typically comprise from about 0.001% to about 5%, preferably 0.01%–1% by weight of a commercial enzyme preparation. Protease enzymes are usually present in such commercial preparations at levels sufficient to provide from 0.005 to 0.1 Anson units (AU) of activity per gram of composition.

Suitable examples of proteases are the subtilisins which are obtained from particular strains of *B. subtilis* and *B. licheniformis*. Another suitable protease is obtained from a strain of Bacillus, having maximum activity throughout the pH range of 8–12, developed and sold by Novo Industries A/S as ESPERASE®. The preparation of this enzyme and analogous enzymes is described in British Patent Specification No. 1,243,784 of Novo. Proteolytic enzymes suitable for removing protein-based stains that are commercially available include those sold under the tradenames ALCALASE® and SAVINASE® by Novo Industries A/S (Denmark) and MAXATASE® by International Bio-Synthetics, Inc. (The Netherlands). Other proteases include Protease A (see European Patent Application 130,756, published Jan. 9, 1985) and Protease B (see European Patent Application Serial No. 87303761.8, filed Apr. 28, 1987, and European Patent Application 130,756, Bott et al, published Jan. 9, 1985).

An especially preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76 in combination with one or more amino acid residue positions equivalent to those selected from the group consisting of +99, +101, +103, +107 and +123 in Bacillus amyloliquefaciens subtilisin as described in the patent applications of A. Baeck, C. K. Ghosh, P. P. Greycar, R. R. Bott and L. J. Wilson, entitled "Protease-Containing Cleaning Compositions" having U.S. Ser. No. 08/136,797 (P&G Case 5040), and "Bleaching Compositions Comprising Protease Enzymes" having U.S. Ser. No. 08/136,626.

Amylases include, for example, α-amylases described in British Patent Specification No. 1,296,839 (Novo), RAPIDASE®, International Bio-Synthetics, Inc. and TERMAMYL®, Novo Industries.

Cellulases usable in the present invention include both bacterial or fungal cellulases. Preferably, they will have a pH optimum of between 5 and 9.5. Suitable cellulases are disclosed in U.S. Pat. No. 4,435,307, Barbesgoard et al, issued Mar. 6, 1984, which discloses fungal cellulase produced from *Humicola insolens* and Humicola strain DSM1800 or a cellulase 212-producing fungus belonging to the genus Aeromonas, and cellulase extracted from the hepatopancreas of a marine mollusk (Dolabella Auricula Solander). Suitable cellulases are also disclosed in GB-A-2.075.028; GB-A-2.095.275 and DE-OS-2.247,832. CAREZYME® (Novo) is especially useful.

Suitable lipase enzymes for detergent use include those produced by microorganisms of the Pseudomonas group, such as *Pseudomonas stutzeri* ATCC 19.154, as disclosed in British Patent 1,372,034. See also lipases in Japanese Patent Application 53,20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Other commercial lipases include Amano-CES, lipases ex *Chromobacter viscosum*, e.g. *Chromobacter viscosum* var. *lipolyticum* NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli*. The LIPOLASE® enzyme derived from *Humicola lanuginosa* and commercially available from Novo (see also EPO 341,947) is a preferred lipase for use herein.

Peroxidase enzymes can be used in combination with oxygen sources, e.g., percarbonate, perborate, persulfate, hydrogen peroxide, etc. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813, published Oct. 19, 1989, by O. Kirk, assigned to Novo Industries A/S.

A wide range of enzyme materials and means for their incorporation into synthetic detergent compositions are also disclosed in U.S. Pat. No. 3,553,139, issued Jan. 5, 1971. to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

Polymeric Soil Release Agent—Any polymeric soil release agent known to those skilled in the art can optionally be employed in the compositions and processes of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

The polymeric soil release agents useful herein especially include those soil release agents having: (a) one or more nonionic hydrophile components consisting essentially of (i) polyoxyethylene segments with a degree of polymerization of at least 2, or (ii) oxypropylene or polyoxypropylene segments with a degree of polymerization of from 2 to 10, wherein said hydrophile segment does not encompass any oxypropylene unit unless it is bonded to adjacent moieties at each end by ether linkages, or (iii) a mixture of oxyalkylene units comprising oxyethylene and from 1 to about 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least about 25% oxyethylene units and more preferably, especially for such components having about 20 to 30 oxypropylene units, at least about 50% oxyethylene units; or (b) one or more hydrophobe components comprising (i) $C_3$ oxyalkylene terephthalate segments, wherein, if said hydrophobe components also comprise oxyethylene terephthalate, the ratio of oxyethylene terephthalate:$C_3$ oxyalkylene terephthalate units is about 2:1 or lower, (ii) $C_4$–$C_6$ alkylene or oxy $C_4$–$C_6$ alkylene segments, or mixtures therein, (iii) poly(vinyl ester) segments, preferably polyvinyl acetate), having a degree of polymerization of at least 2, or (iv) $C_1$–$C_4$ alkyl ether or $C_4$ hydroxyalkyl ether substituents, or mixtures therein, wherein said substituents are present in the form of $C_1$–$C_4$ alkyl ether or $C_4$ hydroxyalkyl ether cellulose derivatives, or mixtures therein, and such cellulose derivatives are amphiphilic, whereby they have a sufficient level of $C_1$–$C_4$ alkyl ether and/or $C_4$ hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a)(i) will have a degree of polymerization of from about 200, although higher levels can be used, preferably from 3 to about 150, more preferably from 6 to about 100. Suitable oxy $C_4$–$C_6$ alkylene hydrophobe segments include, but are not limited to, end-caps of polymeric soil release agents such as $MO_3S(CH_2)_nOCH_2CH_2O$—, where M is sodium and n is an integer from 4–6, as disclosed in U.S. Pat. No. 4,721,580, issued Jan. 26, 1988 to Gosselink.

Polymeric soil release agents useful in the present invention also include cellulosic derivatives such as hydroxyether cellulosic polymers, copolymeric blocks of ethylene terephthalate or propylene terephthalate with polyethylene oxide or polypropylene oxide terephthalate, and the like. Such agents are commercially available and include hydroxyethers of cellulose such as METHOCEL (Dow). Cellulosic soil release agents for use herein also include those selected from the group consisting of $C_1$–$C_4$ alkyl and $C_4$ hydroxyalkyl cellulose; see U.S. Pat. No. 4,000,093, issued Dec. 28, 1976 to Nicol, et al.

Soil release agents characterized by poly(vinyl ester) hydrophobe segments include graft copolymers of poly(vinyl ester), e.g., $C_1$–$C_6$ vinyl esters, preferably poly(vinyl acetate) grafted onto polyalkylene oxide backbones, such as polyethylene oxide backbones. See European Patent Application 0 219 048, published Apr. 22, 1987 by Kud, et al. Commercially available soil release agents of this kind include the SOKALAN type of material, e.g., SOKALAN HP-22, available from BASF (West Gemany).

One type of preferred soil release agent is a copolymer having random blocks of ethylene terephthalate and polyethylene oxide (PEO) terephthalate. The molecular weight of this polymeric soil release agent is in the range of from about 25,000 to about 55,000. See U.S. Pat. No. 3,959,230 to Hays, issued May 25, 1976 and U.S. Pat. No. 3,893,929 to Basadur issued Jul. 8, 1975.

Another preferred polymeric soil release agent is a polyester with repeat units of ethylene terephthalate units contains 10–15% by weight of ethylene terephthalate units together with 90–80% by weight of polyoxyethylene terephthalate units, derived from a polyoxyethylene glycol of average molecular weight 300–5,000. Examples of this polymer include the commercially available material ZELCON 5126 (from Dupont) and MILEASE T (from ICI). See also U.S. Pat. No. 4,702,857, issued Oct. 27, 1987 to Gosselink.

Another preferred polymeric soil release agent is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451, issued Nov. 6, 1990 to J. J. Scheibel and E. P. Gosselink. Other suitable polymeric soil release agents include the terephthalate polyesters of U.S. Pat. No. 4,711,730, issued Dec. 8, 1987 to Gosselink et al, the anionic end-capped oligomeric esters of U.S. Pat. No. 4,721,580, issued Jan. 26, 1988 to Gosselink, and the block polyester oligomeric compounds of U.S. Pat. No. 4,702,857, issued Oct. 27, 1987 to Gosselink.

Preferred polymeric soil release agents also include the soil release agents of U.S. Pat. No. 4,877,896, issued Oct. 31, 1989 to Maldonado et al, which discloses anionic, especially sulfoaroyl, end-capped terephthalate esters.

Still another preferred soil release agent is an oligomer with repeat units of terephthaloyl units, sulfoisoterephthaloyl units, oxyethyleneoxy and oxy-1,2-propylene units. The repeat units form the backbone of the oligomer and are preferably terminated with modified isothionate end-caps. A particularly preferred soil release agent of this type comprises about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate. Said soil release agent also comprises from about 0.5% to about 20%, by weight of the oligomer, of a crystalline-reducing stabilizer, preferably selected from the group consisting of xylene sulfonate, cumene sulfonate, toluene sulfonate, and mixtures thereof.

If utilized, soil release agents will generally comprise from about 0.01% to about 10.0%, by weight, of the detergent compositions herein, typically from about 0.1% to about 5%, preferably from about 0.2% to about 3.0%.

Other Ingredients—Detersive ingredients or adjuncts optionally included in the instant compositions can include one or more materials for assisting or enhancing cleaning performance, treatment of the substrate to be cleaned, or designed to improve the aesthetics of the compositions. Such materials are further illustrated in U.S. Pat. No. 3,936, 537, Baskerville et al. Adjuncts which can also be included in compositions of the present invention, in their conventional art-established levels for use (generally from 0% to about 20% of the detergent ingredients, preferably from about 0.5% to about 10%), include other active ingredients such as dispersant polymers from BASF Corp. or Rohm & Haas; color speckles, anti-tarnish and/or anti-corrosion agents, dyes, fillers, optical brighteners, germicides, alkalinity sources, hydrotropes, anti-oxidants, enzyme stabilizing agents, perfumes, solubilizing agents, clay soil removal/anti-redeposition agents, carriers, processing aids, pigments, solvents for liquid formulations, fabric softeners, static control agents, solid fillers for bar compositions, etc. Dye transfer inhibiting agents, including polyamine N-oxides such as polyvinylpyridine N-oxide can be used. Dye-transfer-inhibiting agents are further illustrated by polyvinylpyrrolidone and copolymers of N-vinyl imidazole and N-vinyl pyrrolidone. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, for example, 0.1%–2%, to provide additional suds and to enhance grease removal performance.

Brightener—Any optical brighteners, fluorescent whitening agents or other brightening or whitening agents known in the art can be incorporated in the instant compositions when they are designed for fabric treatment or laundering, at levels typically from about 0.05% to about 1.2%, by weight, of the detergent compositions herein. Commercial optical brighteners which may be useful in the present invention can be classified into subgroups, which include, but are not necessarily limited to, derivatives of stilbene, pyrazoline, coumarin, carboxylic acids, methinecyanines, dibenzothiophene-5,5-dioxide, azoles, 5- and 6-membered-ring heterocyclic brighteners, this list being illustrative and non-limiting. Examples of such brighteners are disclosed in "The Production and Application of Fluorescent Brightening Agents", M. Zahradnik, Published by John Wiley & Sons, New York (1982).

Specific examples of optical brighteners which are useful in the present compositions are those identified in U.S. Pat. No. 4,790,856, issued to Wixon on Dec. 13, 1988. These brighteners include the PHORWHITE series of brighteners from Verona. Other brighteners disclosed in this reference include: Tinopal UNPA, Tinopal CBS and Tinopal 5BM; available from Ciba-Geigy; Artic White CC and Artic White CWD, available from Hilton-Davis, located in Italy; the 2-(4-styryl-phenyl)-2H-naphthol[1,2-d]triazoles; 4,4'-bis-(1,2,3-triazol-2-yl)-stilbenes; 4,4'-bis(styryl)bisphenyls; and the aminocoumarins. Specific examples of these brighteners include 4-methyl-7-diethyl-aminocoumarin; 1,2-bis(-benzimidazol-2-yl)ethylene; 2,5-bis(benzoxazol-2-yl) thiophene; 2-styryl-napth-[1,2-d]oxazole; and 2-(stilbene-4-yl)-2H-naphtho-[1,2-d]triazole. See also U.S. Pat. No. 3,646,015, issued Feb. 29, 1972 to Hamilton. Anionic brighteners are typically preferred herein.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT® D10, Degussa) is admixed with a proteolytic enzyme solution containing 3%–5% of $C_{13-15}$ ethoxylated alcohol (EO 7) nonionic surfactant. Typically, the enzyme/surfactant solution is 2.5× the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Liquid or gel compositions can contain some water and other fluids as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers.

pH Variation

Certain bleaching compositions herein among the generally encompassed liquid (easily flowable or gel forms) and solid (powder, granule or tablet) forms, especially bleach additive compositions and hard surface cleaning compositions, may be formulated such that the pH is acidic during storage and alkaline during use in aqueous cleaning operations. Automatic dishwashing compositions, other than rinse aids, which may be acidic, will typically have an aqueous solution pH greater than 7. Many compositions will be buffered, i.e., they are relatively resistant to pH drop in the presence of acidic soils. However, other compositions herein may have exceptionally low buffering capacity, or may be substantially unbuffered. Techniques for controlling or varying pH at recommended usage levels more generally include the use of not only buffers but additional alkalis, acids, pH-jump systems, dual compartment containers, etc., and are well known to those skilled in the art. Typical compositions are useful from about 5° C. to the boil for a variety of cleaning and bleaching operations.

Bleaching compositions in granular form typically limit water content, for example to less than about 7% free water, for best storage stability.

Storage stability of bleach compositions can be further enhanced by limiting the content in the compositions of adventitious redox-active substances such as rust and other traces of transition metals in undesirable form. Certain bleaching compositions may moreover be limited in their total halide ion content, or may have any particular halide, e.g., bromide, substantially absent. Bleach stabilizers such as stannates can be added for improved stability and liquid formulations may be substantially nonaqueous if desired.

The following examples illustrate the bleach activators of the invention, intermediates for making same and bleaching, bleach additive, and cleaning compositions which can be prepared using the bleach activators, but are not intended to be limiting thereof. All materials in the Examples satisfy the functional limitations herein.

EXAMPLE I

N-benzoyl-3-oxomorpholine:

A 500 ml, three neck, round bottom flask is fitted with a condenser, a motorized stirrer with a glass bearing, glass rod, and a Teflon™ stir paddle, a thermometer, and a temperature control device (Therm-O-Watch™, $I^2R$). To this reaction flask is added 200 ml of p-dioxane (Baker), and 2-aminoethanol (Aldrich, 62.0 g, 1.015 moles). The reaction temperature is taken up to 85° C. under argon, and sodium metal (Aldrich, 21.4 g, 0.931 moles) is added to the reaction pot. After heating for about 18 hours the sodium is still not fully dissolved under these conditions. Therefore, additional 2-aminoethanol (24.8 g) is added to the reaction in two equal increments spaced about four hours apart. The reaction solution becomes homogeneous after the second addition of aminoethanol and is allowed to cool to room temperature, at which point it becomes a cloudy suspension. The condenser is replaced with an addition funnel, to which is added chloroacetic acid (Aldrich, 40.0 g, 0.423 moles) as a 50% solution in p-dioxane. The reaction mixture is cooled in an ice/water bath and the chloroacetic acid solution is added dropwise into the flask such that the reaction temperature remains below 25° C. After the addition is complete, the reaction mixture is stirred for several minutes and then methanesulfonic acid (20.3 g) is added to the reaction and the mixture is stripped of excess amine and p-dioxane on a Kugelrohr apparatus (Aldrich) at a reduced pressure of 2 mmHg. The temperature is about 100° for 2 hours and is subsequently 150° C. for about 0.5 hours. The solid left in the distillation pot is taken up in water to form a 50% solution. This is adjusted to pH 7 with concentrated HCl. The flask is now put back on a Kugelrohr apparatus at 2 mmHg and 160° C. Over the course of 2 hours, the temperature is slowly raised to 190° C. as white crystals and water collect in an attached receiving trap. The product of this step is charged with about 20 ml of additional water and is extracted twice with 40 ml portions of dichloromethane. The water layer is then saturated with sodium chloride and is extracted again with dichloromethane. The three organic extracts are combined, dried over anhydrous magnesium sulfate, and stripped on a rotary evaporator (Büchi) at 40° C. under aspirator vacuum to leave 9 g of white 3-oxomorpholine crystals.

A 100 ml, three neck round bottom flask is equipped with a stir bar, a condenser, an addition funnel, a thermometer, and a temperature control device (Therm-O-Watch™, I²R). To this reaction flask is added the 3-oxomorpholine synthesized above (5.5 g, 0.054 moles), triethylamine (Aldrich, 6.0 g, 0.059 moles), and toluene (Baker, 15.0 g). To the addition funnel is added benzoyl chloride (Aldrich, 7.6 g, 0.054 moles). The reaction is heated to 90° C. under argon, and the benzoyl chloride is charged dropwise into the flask. After the addition is complete, the reaction is heated under reflux for 10 hours under argon as a white precipitate forms. The reaction mixture is then cooled and the precipitate is removed by vacuum filtration. Solvent is stripped from the resulting filtrate on a Kugelrohr apparatus at 2 mmHg and 70° C. for 1 hour to obtain the desired N-benzoyl-3-oxomorpholine as an oil.

EXAMPLE II

N-Benzoyl-2-methyl-3-oxomorpholine:

Synthesized as for N-benzoyl-3-oxomorpholine (Example I) using 2-chloropropionic acid (Aldrich) in place of chloroacetic acid.

EXAMPLE III

N-Benzoyl-4-oxacaprolactam:

Synthesized as for N-benzoyl-3-oxomorpholine (Example I) using 3-aminopropanol (Aldrich) in place of 2-aminoethanol.

EXAMPLE IV

N-Benzoyl-2-chloro-3-oxomorpholine:

Synthesized by the method of O'Neill and Tull (U.S. Pat. No. 2,877,220, Mar. 10, 1959) using N-benzoyl-3-oxomorpholine (Example I) in place of N-benzoylcaprolactam.

EXAMPLE V

N-Nonanoyl-3-oxomorpholine:

Synthesized as for N-benzoyl-3-oxomorpholine (Example I) using nonanoyl chloride (Aldrich) in place of benzoyl chloride.

EXAMPLE VI

N-Benzoyl-3-chlorocaprolactam:

Synthesized by the method of O'Neill and Tull (U.S. Pat. No. 2,877,220, Mar. 10, 1959). In an alternative preparation, N-benzoyl-3-chlorocaprolactam is synthesized as for N-benzoyl-3-oxomorpholine (Example I) using 3-chlorocaprolactam (prepared as described in Francis, et al. *J. Am. Chem. Soc.* 1958, 80, 6238) in place of 3-oxomorpholine.

EXAMPLE VII

N-Benzoyl-3-methoxycaprolactam:

3-Methoxycaprolactam was prepared from 3-chlorocaprolactam (prepared as described in Francis, et al. *J. Am. Chem. Soc.* 1958, 80, 6238) and sodium methoxide according to the method of Kondelikova, et al. (*Collect. Czech. Chem. Commun.* 1971, 36(9), 3391). The desired product N-benzoyl-3-methoxycaprolactam is synthesized as for N-benzoyl-3-oxomorpholine (Example I) using 3-methoxycaprolactam in place of morpholin-3-one.

EXAMPLE VIII

N-Octanoyl-3-methoxycaprolactam:

Synthesized as for N-benzoyl-3-methoxycaprolactam (Example VII) using octanoyl chloride (Aldrich) in place of benzoyl chloride.

EXAMPLE IX

N-Benzoyl-3,3-dichlorocaprolactam:

Synthesized as for N-benzoyl-3-chlorocaprolactam (Example VI) using 3,3-dichlorocaprolactam (prepared from caprolactam according to *J. Am. Chem. Soc.* 1958, 80, 6238) in place of 3-chlorocaprolactam.

EXAMPLE X

N-Nonanoyl-3,3-dichlorocaprolactam:

Synthesized as for N-benzoyl-3,3-chlorocaprolactam (Example IX) using nonanoyl chloride (Aldrich) in place of benzoyl chloride.

EXAMPLE XI

N-(4-Nitrobenzoyl)-3-chlorocaprolactam:

Synthesized as in the alternative preparation for N-benzoyl-3-chlorocaprolactam (Example VI) using 4-nitrobenzoyl chloride in place of benzoyl chloride.

EXAMPLE XII

N-Benzoyl-3-chlorovalerolactam:

3-Chlorovalerolactam is synthesized as for 3-chlorocaprolactam (prepared from caprolactam according to *J. Am. Chem. Soc.* 1958, 80, 6238) using valerolactam in place of caprolactam. Thereafter, the title compound is synthesized as for N-benzoyl-3-chlorocaprolactam (Example VI) using 3-chlorovalerolactam in place of 3-chlorocaprolactam.

The structures of the alpha-modified lactam bleach activators of Examples I–XII are shown below:

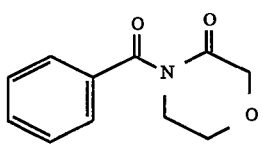

I

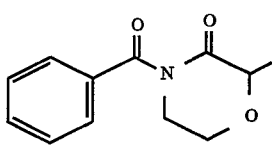

II

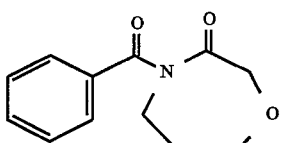

III

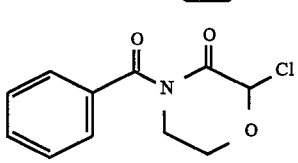

IV

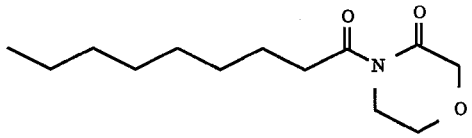
V

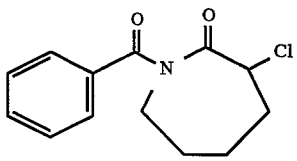
VI

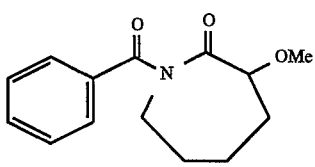
VII

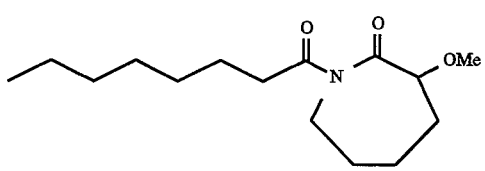
VIII

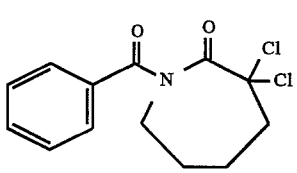
IX

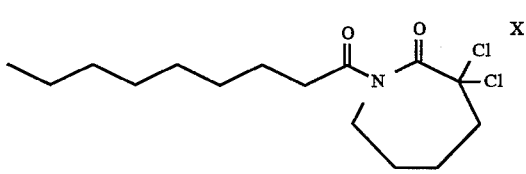
X

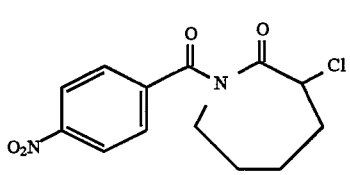
XI

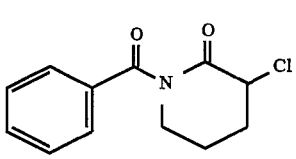
XII

EXAMPLE XIII

Bleaching and/or cleaning compositions having the form of granular laundry detergents are exemplified as follows. In the examples hereinafter unless otherwise specifically indicated, the term "bleach activator" refers to one or more alpha-modified lactam bleach activators forming an essential component of the present invention.

| INGREDIENT | A % | B % | C % | D % | E % |
|---|---|---|---|---|---|
| Bleach Activator* | 5 | 5 | 3 | 3 | 8 |
| Sodium Percarbonate | 0 | 0 | 19 | 21 | 0 |
| Sodium Perborate monohydrate | 21 | 0 | 0 | 0 | 20 |
| Sodium Perborate tetrahydrate | 12 | 21 | 0 | 0 | 0 |
| Tetraacetylethylene-diamine | 0 | 0 | 0 | 1 | 0 |
| Nonanoyloxybenzene-sulfonate | 0 | 0 | 3 | 0 | 0 |
| Linear alkylbenzene-sulfonate | 7 | 11 | 19 | 12 | 8 |
| Alkyl ethoxylate (C45E7) | 4 | 0 | 3 | 4 | 6 |
| Zeolite A | 20 | 20 | 7 | 17 | 21 |
| SKS-6 ® silicate (Hoechst) | 0 | 0 | 11 | 11 | 0 |
| Trisodium citrate | 5 | 5 | 2 | 3 | 3 |
| Acrylic Acid/Maleic Acid copolymer | 4 | 0 | 4 | 5 | 0 |
| Sodium polyacrylate | 0 | 3 | 0 | 0 | 3 |
| Diethylenetriamine penta(methylene phosphonic acid) | 0.4 | 0 | 0.4 | 0 | 0 |
| DTPA | 0 | 0.4 | 0 | 0 | 0.4 |
| EDDS | 0 | 0 | 0 | 0.3 | 0 |
| Carboxymethyl-cellulose | 0.3 | 0 | 0 | 0.4 | 0 |
| Protease | 1.4 | 0.3 | 1.5 | 2.4 | 0.3 |
| Lipolase | 0.4 | 0 | 0 | 0.2 | 0 |
| CAREZYME | 0.1 | 0 | 0 | 0.2 | 0 |
| Anionic soil release polymer | 0.3 | 0 | 0 | 0.4 | 0.5 |
| Dye transfer inhibiting polymer | 0 | 0 | 0.3 | 0.2 | 0 |
| Carbonate | 16 | 14 | 24 | 6 | 23 |
| Silicate | 3.0 | 0.6 | 12.5 | 0 | 0.6 |
| Sulfate, Water, Perfume, Colorants | to 100 | to 100 | to 100 | to 100 | to 100 |

*Bleach activator according to any of Examples I-XII

Any of the above compositions is used to launder fabrics under either "high soil" or "low soil" conditions. "High soil" conditions. In a first suitable mode, consumer bundles of heavily soiled fabrics can be used, the soil level being sufficiently high that when a portion of the composition is dissolved in the presence of tap-water together with the soiled fabrics in a U.S. domestic washing-machine, the pH of the wash water is in the range from about pH 6.5 to about 9.5, more typically from about 7 to about 9.5. Alternatively, it is convenient for testing purposes when heavily soiled fabrics are unavailable, to use the following procedure: the pH of the wash bath after dissolution of product and addition of the test fabrics is adjusted using aqueous HCl such that the pH is in the range from about pH 6.5 to about 9.5. The test fabrics are a lightly soiled or clean bundle of consumer fabrics; additional test swatches of fabric comprising bleachable stains are typically added. In general in the present example, the product usage is low, typically about 1000 ppm concentration of the composition, in the wash.

The fabrics are washed at about 40° C. with excellent results, particularly with respect to bleaching as compared with otherwise identical compositions in which TAED, NOBS or benzoylcaprolactam are used at equal weight as a replacement for the *-identified bleach activator. The alpha-modified lactam bleach activators provide superior results compared with controls in which TAED is substituted for the entirety of the alpha-modified lactam bleach activator, and are preferred.

Additional granular laundry detergents having nonionic surfactant systems are exemplified by the following formulations; they are tested as described supra.

| INGREDIENT | F % | G % | H % | I % |
|---|---|---|---|---|
| Bleach Activator* | 5 | 3 | 6 | 4.5 |
| Sodium Percarbonate | 20 | 21 | 21 | 21 |
| Tetraacetylethylenediamine | 0 | 6 | 0 | 0 |
| Nonanoyloxybenzenesulfonate | 4.5 | 0 | 0 | 4.5 |
| Alkyl ethoxylate (C45E7) | 2 | 5 | 5 | 5 |
| N-cocoyl N-methyl glucamine | 0 | 4 | 5 | 5 |
| Zeolite A | 6 | 5 | 7 | 7 |
| SKS-6® silicate (Hoechst) | 12 | 7 | 10 | 10 |
| Trisodium citrate | 8 | 5 | 3 | 3 |
| Acrylic Acid/Maleic Acid co-polymer (partially neutralized) | 7 | 5 | 7 | 8 |
| Diethylenetriamine penta-(methylene phosphonic acid) | 0.4 | 0 | 0 | 0 |
| EDDS | 0 | 0.3 | 0.5 | 0.5 |
| Carboxymethylcellulose | 0 | 0.4 | 0 | 0 |
| Protease | 1.1 | 2.4 | 0.3 | 1.1 |
| Lipolase | 0 | 0.2 | 0 | 0 |
| CAREZYME | 0 | 0.2 | 0 | 0 |
| Anionic soil release polymer | 0.5 | 0.4 | 0.5 | 0.5 |
| Dye transfer inhibiting polymer | 0.3 | 0.02 | 0 | 0.3 |
| Carbonate | 21 | 10 | 13 | 14 |
| Sulfate, Water, Perfume, Colorants | to 100 | to 100 | to 100 | to 100 |

*Bleach activator according to any of Examples I to XII.

EXAMPLE XIV

This Example illustrates cleaning compositions having bleach additive form, more particularly, liquid bleach additive compositions in accordance with the invention.

| Ingredients | A wt % | B wt % | C wt % | D wt % |
|---|---|---|---|---|
| NEODOL 91-10[1] | 6 | 5 | 7 | 4 |
| NEODOL 45-7[1] | 6 | 5 | 5 | 8 |
| NEODOL 23-2[1] | 3 | 5 | 3 | 3 |
| DEQUEST 2060[2] | 0.5 | 0.5 | 1.0 | 1.0 |
| Bleach Activator[3] | 6 | 6 | 4 | 7 |
| Citric Acid | 0.5 | 0.5 | 0.5 | 0.5 |
| NaOH | to pH 4 | to pH 4 | to pH 4 | to pH 4 |
| Hydrogen Peroxide | 7 | 3 | 2 | 7 |
| Water | Balance to 100% | Balance to 100% | Balance to 100% | Balance to 100% |

| Ingredients | E wt % | F wt % | G wt % |
|---|---|---|---|
| Water | to 100% | to 100% | to 100% |
| NEODOL 91-10[1] | 10 | 10 | 10 |
| NEODOL 23-2[1] | 5 | 5 | 5 |
| DEQUEST 2010[2] | 0.5 | 0.5 | 1.0 |
| Bleach Activator[3] | 4 | 4 | 8 |
| Citric Acid | 0.5 | 0.5 | 0.5 |
| NaOH | to pH 4 | to pH 4 | to pH 4 |
| Hydrogen Peroxide | 7 | 5 | 5 |

[1]Alkyl ethoxylate available from The Shell Oil Company.
[2]Commercially available from Monsanto Co.
[3]Bleach Activator according to any of Examples I–XII.

The compositions are used as bleach boosting additive (to be used in ADDITION to a bleach OR non-bleach detergent such as TIDE®) in a wash test otherwise similar to that used in Example XIII. The additive composition is used at 1000 ppm, and the commercial detergent is used at 1000 ppm.

EXAMPLE XV

This Example illustrates cleaning compositions having bleach additive form, more particularly, liquid bleach additive compositions without a hydrogen peroxide source in accordance with the invention.

| Ingredients | A wt % | B wt % | C wt % | D wt % |
|---|---|---|---|---|
| NEODOL 91-10[1] | 6 | 5 | 7 | 10 |
| NEODOL 45-7[1] | 6 | 5 | 5 | 0 |
| NEODOL 23-2[1] | 3 | 5 | 3 | 5 |
| DEQUEST 2060[2] | 0.5 | 0.5 | 1.0 | 1.0 |
| Bleach Activator[3] | 6 | 6 | 4 | 7 |
| Citric Acid | 0.5 | 0.5 | 0.5 | 0.5 |
| NaOH | to pH 4 | to pH 4 | to pH 4 | to pH 4 |
| Water | Balance to 100% | Balance to 100% | Balance to 100% | Balance to 100% |

[1]Alkyl ethoxylate available from The Shell Oil Company.
[2]Commercially available from Monsanto Co.
[3]Bleach Activator according to any of Examples I–XII.

The compositions are used as bleach boosting additive (to be used in ADDITION to a bleach detergent such as TIDE® WITH BLEACH) in a wash test otherwise similar to that used in Example XII. The additive is used at 1000 ppm, and the commercial detergent is used at 1000 ppm.

EXAMPLE XVI

Bleaching compositions having the form of granular laundry detergents are exemplified as follows:

| INGREDIENT | A % | B % | C % | D % | E % |
|---|---|---|---|---|---|
| Bleach Activator* | 5 | 5 | 3 | 3 | 8 |
| Sodium Percarbonate | 0 | 5 | 15 | 0 | 0 |
| Sodium Perborate monohydrate | 5 | 0 | 0 | 10 | 20 |
| Brightener 49 | 0.4 | 0.4 | 0 | 0 | 0 |
| NaOH | 2 | 2 | 2 | 0 | 2 |
| Linear alkylbenzene-sulfonate, partially neutralized | 9 | 9 | 9 | 9 | 9 |
| Alkyl ethoxylate (C25E9) | 7 | 7 | 5 | 4 | 6 |
| Zeolite A | 32 | 20 | 7 | 17 | 21 |
| Acrylic Acid/Maleic Acid copolymer | 0 | 0 | 4 | 5 | 8 |
| Sodium polyacrylate | 0.6 | 0.6 | 0.6 | 0 | 0 |
| Diethylenetriamine penta(methylene phosphonic acid) | 0.5 | 0 | 0.5 | 0 | 1 |
| EDDS | 0 | 0.5 | 0 | 0.5 | 0 |
| Protease | 1 | 1 | 1.5 | 2.4 | 0.3 |
| Lipolase | 0 | 0 | 0 | 0.2 | 0 |
| CAREZYME | 0 | 0 | 0 | 0.2 | 0 |
| Anionic soil release polymer | 0 | 0 | 0.5 | 0.4 | 0.5 |
| Dye transfer inhibiting polymer | 0 | 0 | 0.3 | 0.2 | 0 |
| Soda Ash | 22 | 22 | 22 | 22 | 22 |
| Silicate (2r) | 7.0 | 7.0 | 7.0 | 7.0 | 7.0 |
| Sulfate, Water, Perfume, Colorants | to 100 | to 100 | to 100 | to 100 | to 100 |

*Bleach activator according to any of Examples I–XII

Any of the above compositions is used to launder fabrics under mildly alkaline conditions (pH 7–8). The pH can be adjusted by altering the proportion of acid to Na-salt form of alkylbenzenesulfonate.

Fabrics are washed at about 40° C. using a concentration of about 1000 ppm of the composition with excellent results, particularly with respect to bleaching as compared with otherwise identical compositions in which TAED or NOBS are used at equal weight as a replacement for the essential alpha-modified lactam bleach activator.

EXAMPLE XVII

A cleaning composition designed for use as a granular bleach additive is as follows:

| Ingredient | % (wt.) |
|---|---|
| Bleach Activator* | 7.0 |
| Sodium Perborate (monohydrate) | 20.0 |
| Chelant (DTPA, acid form) | 10.0 |
| Citric Acid (coated) | 20.0 |
| Sodium Sulfate | Balance |

*Bleach Activator according to any of Examples I-XII.

In an alternate embodiment, the composition is modified by replacing the sodium perborate with sodium percarbonate.

EXAMPLE XVIII

Cleaning compositions having liquid form especially useful for cleaning bathtubs and shower tiles without being harsh on the hands are as follows:

| | % (wt.) | |
|---|---|---|
| Ingredient | A | B |
| Bleach Activator* | 7.0 | 5.0 |
| Hydrogen Peroxide | 10.0 | 10.0 |
| $C_{12}AS$, acid form, partially neutralized | 5.0 | 5.0 |
| $C_{12-14}AE_3S$, acid form, partially neutralized | 1.5 | 1.5 |
| $C_{12}$ Dimethylamine N-Oxide | 1.0 | 1.0 |
| DEQUEST 2060 | 0.5 | 0.5 |
| Citric acid | 5.5 | 6.0 |
| Abrasive (15-25 micron) | 15.0 | 0 |
| HCl | to pH 4 | |
| Filler and water | Balance to 100% | |

*Bleach Activator according to any of Examples I-XII.

EXAMPLE XIX

A cleaning composition having the form of a granular automatic dishwashing detergent composition with activated hydrogen peroxide source as bleaching system comprises the following ingredients:

| INGREDIENT | A wt % | B wt % | C wt % | D wt % |
|---|---|---|---|---|
| Bleach Activator (See Note 1) | 3 | 4.5 | 2.5 | 4.5 |
| Sodium Perborate Monohydrate (See Note 2) | 1.5 | 0 | 1.5 | 0 |
| Sodium Percarbonate (See Note 2) | 0 | 1.2 | 0 | 1.2 |
| Amylase (TERMAMYL ® from NOVO) | 1.5 | 2 | 2 | 2 |
| Dibenzoyl Peroxide | 0 | 0 | 0.8 | 0 |
| Transition Metal Bleach Catalyst (See Note 3) | 0 | 0.1 | 0.1 | 0 |
| Protease (SAVINASE ® 12 T, NOVO, 3.6% active protein) | 2.5 | 2.5 | 2.5 | 2.5 |
| Trisodium Citrate Dihydrate (anhydrous basis) | 7 | 15 | 15 | 15 |
| Citric Acid | 14 | 0 | 0 | 0 |
| Sodium Bicarbonate | 15 | 0 | 0 | 0 |
| Sodium Carbonate, anhydrous | 20 | 20 | 20 | 20 |
| BRITESIL H2O ®, PQ Corp. (as $SiO_2$) | 7 | 8 | 7 | 5 |
| Diethylenetriaminepenta- (methylenephosphonic acid), Na | 0 | 0 | 0 | 0.2 |
| Hydroxyethyldiphosphonate (HEDP), Sodium Salt | 0 | 0.5 | 0 | 0.5 |
| Ethylenediaminedisuccinate, Trisodium Salt | 0.1 | 0.3 | 0 | 0 |
| Dispersant Polymer (ACCUSOL 480N) | 6 | 5 | 8 | 10 |
| Nonionic Surfactant (LF404, BASF) | 2.5 | 1.5 | 1.5 | 1.5 |
| Paraffin (WINOG 70 ®) | 1 | 1 | 1 | 0 |
| Benzotriazole | 0.1 | 0.1 | 0.1 | 0 |
| Sodium Sulfate, water, minors BALANCE TO: | 100% | 100% | 100% | 100% |

Note 1: Bleach Activator according to any of Examples I-XII.
Note 2: These hydrogen peroxide sources are expressed on a weight % available oxygen basis. To convert to a basis of percentage of the total composition, divide by about 0.15.
Note 3: Transition Metal Bleach Catalyst: MnEDDS according to U.S. Application Ser. No. 08/210,186, filed March 17, 1994.

EXAMPLE XX

A commercial rinse-aid block sold as "Jet-Dry" is modified as follows: The rinse aid block and about 5%-20% of a bleach activator according to any of Examples I-XII are co-melted, mixed and resolidified into block form, optionally with the inclusion of a transition-metal-containing bleach catalyst. The resulting cleaning composition is used in an automatic dishwashing appliance following conventional usage instructions and using a sodium perborate-containing granular automatic dishwashing detergent, with excellent spotting/filming and stain removal results.

EXAMPLE XXI

Liquid bleaching compositions for cleaning typical household surfaces are as follows. The hydrogen peroxide is separated as an aqueous solution from the other components by any suitable means, such as a dual-chamber container.

| Component | A (wt %) | B (wt %) |
|---|---|---|
| $C_{8-10}E_6$ nonionic surfactant | 20 | 15 |
| $C_{12-13}E_3$ nonionic surfactant | 4 | 4 |
| $C_8$ alkyl sulfate anionic surfactant | 0 | 7 |
| $Na_2CO_3$/$NaHCO_3$ | 1 | 2 |
| $C_{12-18}$ Fatty Acid | 0.6 | 0.4 |
| Hydrogen peroxide | 7 | 7 |
| Bleach Activator* | 7 | 7 |
| DEQUEST 2060** | 0.05 | 0.05 |
| $H_2O$ | Balance to 100 | Balance to 100 |

*Bleach Activator according to any of Examples I-XII.
**Commercially available from Monsanto Co.

EXAMPLE XXII

A laundry bar suitable for hand-washing soiled fabrics is prepared by standard extrusion processes and comprises the following:

| Component | Weight % |
| --- | --- |
| Bleach Activator according to any of Examples I-XII | 4 |
| Sodium Perborate Tetrahydrate | 12 |
| $C_{12}$ linear alkyl benzene sulfonate | 30 |
| Phosphate (as sodium tripolyphosphate) | 10 |
| Sodium carbonate | 5 |
| Sodium pyrophosphate | 7 |
| Coconut monoethanolamide | 2 |
| Zeolite A (0.1–10 micron) | 5 |
| Carboxymethylcellulose | 0.2 |
| Polyacrylate (m.w. 1400) | 0.2 |
| Brightener, perfume | 0.2 |
| Protease | 0.3 |
| $CaSO_4$ | 1 |
| $MgSO_4$ | 1 |
| Water | 4 |
| Filler* | Balance to 100% |

*Can be selected from convenient materials such as $CaCO_3$, talc, clay, silicates, and the like. Acidic fillers can be used to reduce pH. Fabrics are washed with the bar with excellent results.

What is claimed is:

1. A cleaning composition comprising:

from about 0.1% to about 30% of a bleach activator having an N-acyl active linkage wherein the nitrogen atom in said linkage is the named N of an N-acyl-3-morpholinone compound, from about 0.1% to about 60% of nonionic surfactant; and from about 0.001% to about 10% of a transition-metal chelant.

2. A cleaning composition comprising:

from about 0.1% to about 30% of a bleach activator having an N-acyl active linkage wherein the nitrogen atom in said linkage is the named N of an N-acyl-3-morpholinone compound;

from about 0.1% to about 70% of a hydrogen peroxide source; and from about 0.001% to about 10% of a transition-metal chelant.

3. A cleaning composition according to claim 1 or 2 wherein said N-acyl-3-morpholinone bleach activator comprises a moiety RC(O)— which produces a peracid RC(O)—OOH and a 3-morpholinone leaving group, L on perhydrolysis; and said leaving-group, L covalently connects to said moiety RC(O)—; said N-acyl-3-morpholinone bleach activator having a perhydrolysis efficiency coefficient of greater than about 0.10 and a ratio of $k_P/k_{CL}>1$ wherein $k_P$ is the rate constant for perhydrolysis of said N-acyl-3-morpholinone bleach activator and $k_{CL}$ is the rate constant for perhydrolysis under otherwise identical conditions of an unmodified lactam reference compound having the formula:

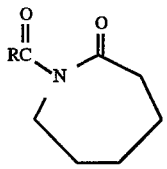

wherein RC(O)— is as defined in said moiety of said N-acyl-3-morpholinone bleach activator.

4. A cleaning composition according to claim 3 wherein said N-acyl-3-morpholinone bleach activator has a ratio $k_P/k_D \geq 2$ wherein $k_P$ is said rate constant for perhydrolysis and wherein $k_D$ is the rate constant for formation of a diacylperoxide from said N-acyl-3-morpholinone bleach activator; a ratio $k_P/k_H \geq 1$ wherein $k_P$ is said rate constant for perhydrolysis and wherein $k_H$ is the rate constant for hydrolysis of said N-acyl-3-morpholinone bleach activator, and said rate constant $k_H \leq 10 M^{-1} s^{-1}$.

5. A cleaning composition according to claim 4 wherein $k_P/k_H \geq 2$ and $k_P/k_D \geq 5$.

6. A cleaning composition according to claim 3 wherein R is selected such that the difference in aqueous $pK_a$ between acetic acid and the carboxylic acid analog, RC(O)OH, of said peracid is at least 0.6 and L is selected such that its conjugate acid, HL, has an aqueous $pK_a$ in the range from greater than about 13 to less than about 17, and wherein RC(O)L has a low pH perhydrolysis efficiency coefficient of greater than about 0.20.

7. A cleaning composition according to claim 6 wherein R and L are neutral moieties.

8. A cleaning composition according to claim 3 wherein R is connected to C(O)— in said moiety RC(O)— through a carbon atom which forms part of an aromatic ring.

9. A cleaning composition according to claim 3 wherein R comprises a phenyl or furyl moiety.

10. A cleaning composition according to claim 3 wherein R is a member selected from the group consisting of phenyl, 4-nitrophenyl, 3-chlorophenyl, 3,5-dinitrophenyl, 3,5-dichlorophenyl, 4-(alkylsulfonyl)phenyl, 2-furyl, 3-furyl, 5-nitro-2-furyl and 5-nitro-3-furyl.

11. A cleaning composition according to claim 3 wherein R is a member selected from the group consisting of phenyl, 4-(alkylsulfonyl)phenyl, 2-furyl, 3-furyl, 5-nitro-2-furyl, 5-nitro-3-furyl and mixtures thereof.

12. A cleaning composition according to claim 3 wherein L is a member selected from the group consisting of

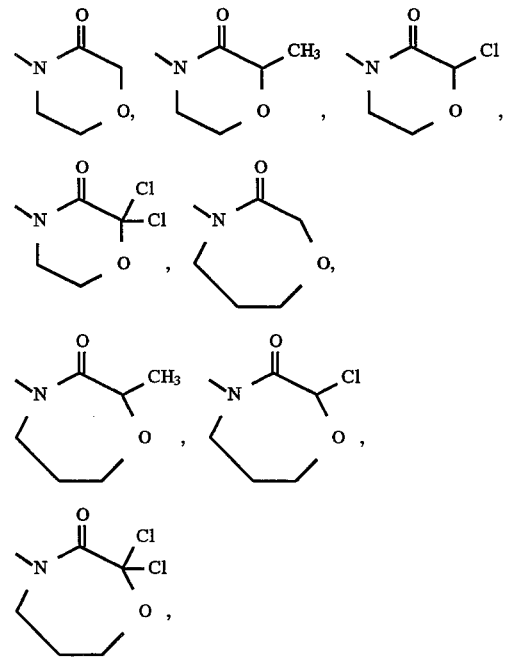

and mixtures thereof.

13. A composition according to claim 3, wherein the activator is N-Benzoyl-3-oxomorpholine.

14. A cleaning composition according to claim 1 which is substantially free from hydrogen peroxide or hydrogen peroxide releasing sources.

15. A cleaning composition according to claim 2 wherein said composition delivers an aqueous pH in the range from about 6.5 to about 9.5 and wherein the level of said source of hydrogen peroxide is sufficient to provide a perhydroxyl ion concentration, as measured at a pH of about 7.5, of about $10^{-4}$ to about $10^{-10}$ molar.

* * * * *